US010457624B2

(12) United States Patent
Sookraj et al.

(10) Patent No.: US 10,457,624 B2
(45) Date of Patent: Oct. 29, 2019

(54) SYSTEMS AND PROCESSES FOR THERMOLYSIS OF POLYLACTONES TO PRODUCE ORGANIC ACIDS

(71) Applicant: Novomer, Inc., Boston, MA (US)

(72) Inventors: Sadesh H. Sookraj, Cambridge, MA (US); Kyle Evan Sherry, Rochester, NY (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/612,884

(22) Filed: Jun. 2, 2017

(65) Prior Publication Data

US 2018/0305289 A1    Oct. 25, 2018

Related U.S. Application Data

(63) Continuation-in-part of application No. 15/494,805, filed on Apr. 24, 2017, now Pat. No. 10,065,914.

(51) Int. Cl.

| C07C 51/377 | (2006.01) |
| B01J 19/00  | (2006.01) |
| B01J 19/18  | (2006.01) |
| B01J 19/24  | (2006.01) |
| C07C 57/04  | (2006.01) |
| C07D 407/12 | (2006.01) |
| C07D 305/12 | (2006.01) |
| C07D 305/14 | (2006.01) |
| C08G 63/78  | (2006.01) |

(52) U.S. Cl.
CPC ......... *C07C 51/377* (2013.01); *B01J 19/0066* (2013.01); *B01J 19/18* (2013.01); *B01J 19/2405* (2013.01); *C07C 57/04* (2013.01); *C07D 305/12* (2013.01); *C07D 305/14* (2013.01); *C07D 407/12* (2013.01); *C08G 63/78* (2013.01); *B01J 2219/00051* (2013.01); *B01J 2219/24* (2013.01)

(58) Field of Classification Search
CPC ................................................... C07C 51/377
See application file for complete search history.

(56) References Cited

U.S. PATENT DOCUMENTS

| 2,361,036 | A |   | 10/1944 | Kun et al. |
| 3,002,017 | A |   | 9/1961  | Wearsch et al. |
| 3,169,945 | A |   | 2/1965  | Fritz et al. |
| 3,678,069 | A |   | 7/1972  | Busler |
| 3,954,854 | A |   | 5/1976  | Gehrman et al. |
| 4,317,926 | A |   | 3/1982  | Sato et al. |
| 4,792,620 | A | * | 12/1988 | Paulik .................. B01J 31/0231 560/232 |
| 5,310,948 | A |   | 5/1994  | Drent et al. |
| 5,359,081 | A |   | 10/1994 | Drent et al. |
| 5,648,452 | A |   | 7/1997  | Schechtman et al. |
| 6,133,402 | A |   | 10/2000 | Coates et al. |
| 6,252,110 | B1 |  | 6/2001  | Uemura et al. |
| 6,316,590 | B1 |  | 11/2001 | Coates et al. |
| 6,538,101 | B2 |  | 3/2003  | Coates et al. |
| 6,608,170 | B1 |  | 8/2003  | Coates |
| 6,852,865 | B2 |  | 2/2005  | Coates et al. |
| 6,887,380 | B2 |  | 5/2005  | Lee et al. |
| 7,420,064 | B2 |  | 9/2008  | Luinstra et al. |
| 8,445,703 | B2 |  | 5/2013  | Allen et al. |
| 8,796,475 | B2 |  | 8/2014  | Allen et al. |
| 9,096,510 | B2 |  | 8/2015  | Porcelli et al. |
| 9,115,070 | B2 |  | 8/2015  | Pazicky et al. |
| 9,156,803 | B2 |  | 10/2015 | Allen et al. |
| 9,206,144 | B2 |  | 12/2015 | Allen et al. |
| 9,327,280 | B2 |  | 5/2016  | Lee et al. |
| 9,403,788 | B2 |  | 8/2016  | Lee et al. |
| 9,493,391 | B2 |  | 11/2016 | Allen et al. |
| 9,719,037 | B2 |  | 8/2017  | Sookraj |
| 9,738,784 | B2 |  | 8/2017  | Allen et al. |
| 9,914,689 | B2 |  | 3/2018  | Porcelli et al. |
| 10,065,914 | B1 | | 9/2018  | Ruhl et al. |
| 10,099,988 | B2 | | 10/2018 | Farmer et al. |
| 10,099,989 | B2 | | 10/2018 | Sookraj |

(Continued)

FOREIGN PATENT DOCUMENTS

| EP | 0577206      | 1/1994  |
| EP | 0887334 A1   | 12/1998 |

(Continued)

OTHER PUBLICATIONS

Norskov et al, Nature Chemistry, Towards the Computational Design of Solid Catalysts, 2009, 1, pp. 37-46. (Year: 2009).*
International search report dated Jul. 6, 2018 in application No. PCT/US2018/029060 filed Apr. 24, 2018 (14 pages).
International search report dated Jun. 21, 2018 in application No. PCT/US2018/029067 filed Apr. 24, 2018 (16 pages).
Abe et al., "Effects of Residual Zinc Compounds and Chain-End Structure on Thermal Degradation of Poly($\varepsilon$-caprolactone)", Biomacromolecules, vol. 5, 2004, pp. 1480-1488.
Agostini et al., "Synthesis and Characterization of Poly-$\beta$-Hydroxybutyrate. I. Synthesis of Crystalline DL-Poly-$\beta$-Hydroxybutyrate from DL-$\beta$-Butyrolactone", Journal of Polymer Science, Part A-1, vol. 9, No. 10, 1971, pp. 2775-2787.

(Continued)

*Primary Examiner* — Paul A Zucker
(74) *Attorney, Agent, or Firm* — Morrison & Foerster LLP

(57) ABSTRACT

Reactor systems and processes produce organic acids through thermolysis of polylactones. The reactor systems and processes introduce at least one epoxide reagent and carbon monoxide reagent to at least one reaction vessel through at least one feed stream inlet. The epoxide reagent and carbon monoxide reagent contact at least one carbonylation catalyst to produce at least one beta-lactone intermediate. The beta-lactone intermediate is polymerized with at least one initiator in the presence of a metal cation to produce at least one polylactone product. The polylactone product is heated under thermolysis conditions to produce at least one organic acid product. The processes control the presence of contaminates, impurities, catalytic materials, and/or reagents to provide for highly pure organic acid products.

11 Claims, 4 Drawing Sheets

(56) References Cited

U.S. PATENT DOCUMENTS

| | | |
|---|---|---|
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2005/0014977 A1 | 1/2005 | Drent et al. |
| 2007/0161806 A1 | 7/2007 | Preishuber-Pflugl et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0018574 A1 | 1/2014 | Raith et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0183708 A1 | 7/2015 | Harris et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0354881 A1 | 12/2018 | Farmer et al. |
| 2018/0354882 A1 | 12/2018 | Sookraj |
| 2019/0002385 A1 | 1/2019 | Sookraj et al. |
| 2019/0030520 A1 | 1/2019 | Lee |
| 2019/0031592 A1 | 1/2019 | Sookraj et al. |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | | | |
|---|---|---|---|---|
| JP | 45-19281 Y1 | 8/1970 | | |
| JP | 09169753 A | * 6/1997 | | |
| JP | H09169753 | 6/1997 | | |
| WO | 2010/118128 A1 | 10/2010 | | |
| WO | 2011/100608 A1 | 8/2011 | | |
| WO | WO 2011163309 | 12/2011 | | |
| WO | 2012/030619 A1 | 3/2012 | | |
| WO | 2012/051219 A2 | 4/2012 | | |
| WO | 2012/158573 A1 | 11/2012 | | |
| WO | WO 2013063191 | 5/2013 | | |
| WO | 2013/122905 A1 | 8/2013 | | |
| WO | WO 2013126375 | 8/2013 | | |
| WO | WO-2013126375 A1 | * 8/2013 | ............. | C07C 51/09 |
| WO | 2013/185009 A1 | 12/2013 | | |
| WO | 2014/004858 A1 | 1/2014 | | |
| WO | WO 2014008232 | 1/2014 | | |
| WO | 2015/085295 A2 | 6/2015 | | |
| WO | 2015/138975 A1 | 9/2015 | | |
| WO | 2015/171372 A1 | 11/2015 | | |
| WO | 2015/184289 A1 | 12/2015 | | |
| WO | 2016/015019 A1 | 1/2016 | | |
| WO | 2016/130947 A1 | 8/2016 | | |
| WO | 2016/130977 A1 | 8/2016 | | |
| WO | 2016/130988 A1 | 8/2016 | | |
| WO | 2016/130993 A1 | 8/2016 | | |
| WO | 2016/130998 A1 | 8/2016 | | |
| WO | 2016/131001 A1 | 8/2016 | | |
| WO | 2016/131003 A1 | 8/2016 | | |
| WO | 2016/131004 A1 | 8/2016 | | |
| WO | 2017/023777 A1 | 2/2017 | | |
| WO | 2017/023820 A1 | 2/2017 | | |
| WO | 2017/165323 A1 | 9/2017 | | |
| WO | 2017/165344 A1 | 9/2017 | | |
| WO | 2017/165345 A1 | 9/2017 | | |
| WO | 2018/085251 A1 | 5/2018 | | |
| WO | WO 2018085254 | 5/2018 | | |
| WO | 2018/106824 A1 | 6/2018 | | |
| WO | 2018/136638 A1 | 7/2018 | | |
| WO | 2018/144998 A1 | 8/2018 | | |
| WO | 2018/170006 A1 | 9/2018 | | |
| WO | 2018/200466 A1 | 11/2018 | | |
| WO | 2018/200471 A1 | 11/2018 | | |
| WO | 2019/006366 A1 | 1/2019 | | |
| WO | 2019/006377 A1 | 1/2019 | | |
| WO | 2019/050649 A1 | 3/2019 | | |
| WO | 2019/051184 A1 | 3/2019 | | |
| WO | 2019/070981 A1 | 4/2019 | | |

OTHER PUBLICATIONS

Abe, Hideki, "Thermal Degradation of Environmentally Degradable Poly(Hydroxyalkanoic Acid)s", Macromolecular Bioscience, vol. 6, 2006, pp. 469-486.

"Beta Elimination of Esters in Poly Lactones", Aug. 17, 2017.

Billingham et al., "Polymerization and Copolymerizationof β-Butyrolactone by Aluminium Compounds", Journal of Organometallic Chemistry, vol. 341, No. 1-3, 1988, pp. 83-93.

Church et al., "Carbonylation of Heterocycles by Homogeneous Catalysts", Chemical Communications, vol. 21, No. 7, 2007, pp. 657-674.

Dunn, Erin Whitfield., "Synthesis of Poly(Hydroxyalkanoates): Routes to Poly(3-Hydroxybutyrate) and Poly(3-Hydroxypropionate) from the Carbonylation and Ring-Opening Polymerization of Epoxides", A Dissertation Presented to the Faculty of the Graduate School of Cornell University, Aug. 2012, pp. 1-139.

Garozzo et al., "Primary Thermal Decomposition Processes in Aliphatic Polyesters Investigated by Chemical Ionization Mass Spectrometry", Macromolecules, vol. 19, 1986, pp. 1643-1649.

Gresham et al., "Beta-Propiolactone I. Polymerization Reactions", J. Am. Chem. Soc., vol. 70, 1948, pp. 998-999.

Gresham et al., "Beta-Propiolactone II. Reactions with Salts of Inorganic Acids", J. Am. Chem. Soc., vol. 70, 1948, pp, 999-1001.

Gresham et al., "Beta-Propiolactone III. Reactions with Dithiocarbamic Acids, their Salts and Thiourea.", J. Am. Chem. Soc., vol. 70, 1948, pp. 1001-1002.

Gresham et al., "Beta-Propiolactone IV. Reactions with Salts of Carboxylic Acids", J. Am. Chem. Soc., vol. 70, 1948, pp. 1003-1004.

Gresham et al., "Beta-Propiolactone V. Reaction with Alcohols", J. Am. Chem. Soc., vol. 70, 1948, pp. 1004-1006.

Gross et al., "Polymerization of β-Monosubstituted-β-Propiolactones using Trialkylaluminum-Water Catalytic Systems and Polymer Characterization", Macromolecules, vol. 21, No. 9, 1988, pp. 2657-2668.

Hori et al., "Ring-Opening Polymerization of Optically Active β-Butyrolactone using Distannoxane Catalysts: Synthesis of High-Molecular-Weight Poly (3-Hydroxybutyrate)", Macromolecules, vol. 26, No. 20, 1993, pp. 5533-5534.

International Search Report and Written Opinion received for PCT Patent Application No. PCT/US2016/044772, dated Nov. 8, 2016, 17 pages.

International Search Report and Written Opinion received for PCT Patent Application No. PCT/US2016/044927, dated Nov. 8, 2016, 17 pages.

(56) References Cited

OTHER PUBLICATIONS

Iwabuchi et al., "The Thermal Degradation of Poly(Oxycarbonylethylene) (Poly-β-Propiolactone)", Die Makromolekulare Chemie, vol. 165, 1973, pp. 59-72.

Jacobi et al., "Strukturuntersuchung von polyestern durch direkten abbau im massenspektrometer, 4. Polyester und copolyester der milchsäure und glykolsäure", Macromolecular Chemistry and Physics, vol. 179, 1978, pp. 429-436.

Kim et al., "Effect of Metal Compounds on Thermal Degradation Behavior of Aliphatic Poly(Hydroxyalkanoic Acid)s", Polymer Degradation and Stability, vol. 93, 2008, pp. 776-785.

Kim et al., "Effects of Residual Metal Compounds and Chain-End Structure on Thermal Degradation of Poly(3-Hydroxybutyric Acid)", Polymer Degradation and Stability, vol. 91, 2006, pp. 769-777.

Kim et al., "Thermal Degradation Behavior of Poly(4-Hydroxybutyric Acid)", Polymer Degradation and Stability, vol. 91, 2006, pp. 2333-2341.

Kopinke et al., "Thermal Decomposition of Biodegradable Polyesters-I: Poly(β-Hydroxybutyric Acid)", Polymer Degradation and Stability, vol. 52, 1996, pp. 25-38.

Kricheldorf et al., "Strukturuntersuchung von polyestern durch direkten abbau im massenspektrometer", Macromolecular Chemistry and Physics, vol. 179, 1978, pp. 421-427.

Liu et al., "Reducing the Formation of Six-Membered Ring Ester during Thermal Degradation of Biodegradable PHBV to Enhance its Thermal Stability", Polymer Degradation and Stability, vol. 94, 2009, pp. 18-24.

Luderwald et al., "Strukturuntersuchung von Polyestern durch direkten Abbau im Massenspektrometer", 2. Makromol. Chem. vol. 177, 1976, pp. 2093-2111.

Nguyen et al., "Thermal Degradation of Poly(3-Hydroxyalkanoates): Preparation of Well-Defined Oligomers", Biomacromolecules, vol. 3, 2002, pp. 219-224.

Non-Final Office Action received for U.S. Appl. No. 15/494,805, dated Oct. 4, 2017, 16 pages.

Notice of Allowance received for U.S. Appl. No. 15/494,805, dated Feb. 13, 2018, 12 pages.

Notice of Allowance received for U.S. Appl. No. 15/494,805, dated May 23, 2018, 10 pages.

Rieth et al., "Single-Site Beta-Diiminate Zinc Catalysts for the Ring-Opening Polymerization of Beta-Butyrolactone and Beta-Valerolactone to Poly (3-Hydroxyalkanoates)." Journal of the American Chemical Society, vol. 124, No. 51, 2002, pp. 15239-15248.

Schechtman et al., "Chemical Synthesis of Isotactic Poly(3-Hydroxyalkanoates)", Polymer Preprints, Division of Polymer Chemistry, Inc., vol. 40, No. 1, 1999, pp. 508-509.

Sorrell, Thomas N., "Organic Chemistry", University Science Books, 1999.

Tanahashi et al., "Thermal Properties and Stereoregularity of Poly (3-Hydroxybutyrate) Prepared from Optically Active β-Butyrolactone with a Zinc-based Catalyst", Macromolecules, vol. 24, No. 20, 1991, pp. 5732-5733.

Varma-Nair et al., "Heat Capacity and other Thermodynamic Properties of Linear Macromolecules", Journal of Physical and Chemical Reference Data, 1980.

Zhang et al., "Stereochemistry of the Ring-Opening Polymerization of (S)-β-Butyrolactone", Macromolecules, vol. 23, No. 13, 1990, pp. 3206-3212.

Zhu et al., "Polymorphic Crystallization and Melting—Recrystallization Behavior of Poly(3-Hydroxypropionate)", Macromolecules, vol. 38, 2005, pp. 6455-6465.

* cited by examiner

SYSTEMS AND PROCESSES FOR THERMOLYSIS OF POLYLACTONES TO PRODUCE ORGANIC ACIDS

CROSS REFERENCE TO RELATED APPLICATIONS

The present application is a continuation-in-part that claims priority to and the benefit of U.S. Ser. No. 15/494,805, filed Apr. 24, 2017 (issued on Sep. 4, 2018 as U.S. Pat. No. 10,065,914), which is hereby incorporated by reference in its entirety as if fully restated herein.

FIELD OF THE INVENTION

The present invention relates generally to reactor systems and processes for producing organic acids through thermolysis of polylactones. More specifically, the reactor systems and processes are directed to thermolysis of polylactones comprised of epoxide and carbon monoxide monomers. Advantageously, the reactor systems and processes may provide for versatile production of organic acids from renewable epoxides and carbon monoxide feed sources.

BACKGROUND OF THE INVENTION

The term "carbonylation" generally refers to chemical reactions that introduce carbon monoxide molecules into other organic and inorganic substrate molecules. Carbonylation results in a substrate molecule gaining a carbonyl functional group. Carbonylation reactions are important in industrial chemistry and are becoming a more important building block for fine and bulk chemicals. Specifically, catalytic carbonylation of cyclic compounds including epoxides, aziridines, thiiranes, oxetanes, lactones, lactams, and analogous compounds is useful for the synthesis of the ring expanded products of such compounds.

Further commercial and industrial benefit may result in modifying cyclic compounds through a process known as ring opening polymerization which is a form of chain-growth polymerization. In ring opening polymerization, the terminal end of a polymer chain acts as a reactive center where further cyclic monomers can react by opening cyclic rings and forming a longer polymer chain. Under certain conditions, ring-opening polymerization can proceed via radical, anionic or cationic polymerization. Certain beta-lactone molecules, such as beta-butyrolactone, beta-valerolactone, beta-heptanolactone, beta-tridecanolactone, cis-3,4-dimethyloxetan-2-one, 4-(butoxymethyl)-2-oxetanone, 4-[[[(1,1-dimethylethyl)dimethylsilyl]oxy]methyl]-2-oxetanone, and 4-[(2-propen-1-yloxy)methyl]-2-oxetanone, 4-[(benzoyloxy)methyl]-2-oxetanone to name a few, may undergo ring opening polymerization to produce certain polylactones.

Polylactones, including polypropiolactone, polylactide, polyglycolide, and polycaprolactone, may be characterized as biodegradable polymers. Polylactones are generally stable, have low toxicity, and may be easily transported and stored at remote locations. Recent advances in the carbonylation of epoxides—such as in U.S. Pat. No. 6,852,865—and the ring opening polymerization of beta-propiolactone intermediates has provided more efficient synthetic routes to polylactones. The recent advances in the production of polylactones combined with certain physical and chemical properties make the polylactones ideal for many commercial and industrial applications. However, conventional processes may be less effective at producing highly pure polylactones. Certain polylactones may be thermally decomposed through a process known as thermolysis.

Generally, thermolysis is a chemical decomposition process in which heat causes the cleavage of one or more covalent bonds. In at least one mechanism for thermolysis of polymers, heat converts a polymer of chain length n into a polymer of chain length n−1 and produces a molecule of an organic acid.

SUMMARY OF THE INVENTION

There exists a need for innovative reactor systems and processes that produce organic acid products through the production and subsequent thermolysis of polylactone polymers.

One object of the present invention is to provide for the processes which may produce organic acid products.

Another object of the present invention is to provide for the reactor systems which may be configured to produce organic acid products through the processes of the present invention.

In preferred aspects of the present invention, the reactor systems and processes are customizable and/or configurable for production and subsequent thermolysis of polylactones. In preferred aspects of the present invention, the organic acid products may be wholly or partially comprised of reagents from bio-based and/or renewable sources.

In preferred embodiments, the reactor systems and processes may provide for carbonylation of at least one epoxide reagent with at least one carbon monoxide reagent to produce at least one beta-lactone intermediate which undergoes ring opening polymerization to produce at least one polylactone product. Advantageously, the reactor systems and processes of the present invention may produce polylactone products having certain chemical and physical properties beneficial for producing highly pure organic acid thermolysis products.

In preferred embodiments, the reactor systems and processes overcome the deficiencies of conventional systems by providing for carbonylation of a broad range of epoxide reagents with carbon monoxide reagents to form a broad range of beta-lactone intermediates. In preferred aspects of this invention at least a portion of the epoxide reagents and/or carbon monoxide reagents may be derived from bio-based, refinery/chemical waste streams, municipal solid waste, and other renewable sources. Advantageously, the versatile reactor systems and processes of the present invention may be configured to provide a broad range of organic acid products to meet demands driven by environmental concerns, regulatory changes, consumer trends, and/or production costs to name a few.

In certain preferred embodiments, the reactor systems and processes may produce at least one polylactone product and at least one organic acid product by the thermolysis of the at least one polylactone product at one proximate geographic location. In certain other preferred embodiments, the reactor systems and processes may produce at least one polylactone product at a primary geographic location and at least one organic acid product by the thermolysis of the at least one polylactone product at one or more secondary geographic locations. In certain embodiments, the reactor systems and processes may be configured from continuous production of at least one polylactone product and/or production of at least one organic acid product by the thermolysis of the at least one polylactone product.

In preferred embodiments of the present invention, the reactor systems and processes may include at least one reaction vessel defining at least one feed stream inlet and at least one product stream outlet. In certain preferred embodiments, the at least one reaction vessel may define at least one carbonylation chamber, at least one polymerization chamber, at least one thermolysis chamber, and/or at least one separation chamber. In certain preferred embodiments, the at least one reaction vessel may include at least one heater and/or at least one mixer. In certain embodiments, the at least one reaction vessel may be configured for continuous production of at least one beta-lactone intermediate, at least one polylactone product, and/or at least one organic acid product by introducing material to the at least one reaction vessel through the at least one feed stream inlet at a rate approximately equal to the rate at which material is removed through the at least one product stream outlet. In certain embodiments, the at least one reaction vessel may be in the same geographic location such as a building, facility, compound, property, and/or municipality. In certain other embodiments, the at least one reaction vessel may be located at a primary location and one or more secondary locations which may be remote in distance from the primary location.

In preferred embodiments of the present invention, the processes comprise the following steps: introducing at least one epoxide reagent and at least one carbon monoxide reagent to at least one reaction vessel through at least one feed stream inlet; contacting the at least one epoxide reagent and at least one carbon monoxide reagent with at least one carbonylation catalyst to produce at least one beta-lactone intermediate; polymerizing the at least one beta-lactone intermediate with at least one initiator in the presence of a metal cation to produce at least one polylactone product; heating the at least one polylactone product under thermolysis conditions to produce at least one organic acid product. Advantageously, the processes of the present invention may control the presence of contaminates, impurities, catalytic materials, and/or reagents to provide for highly pure organic acid products.

While this disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

BRIEF DESCRIPTION OF THE DRAWINGS

The present invention can be better understood by reading the following detailed description of certain preferred embodiments, reference being made to the accompanying drawings in which.

DETAILED DESCRIPTION OF EMBODIMENTS

Figure 1:
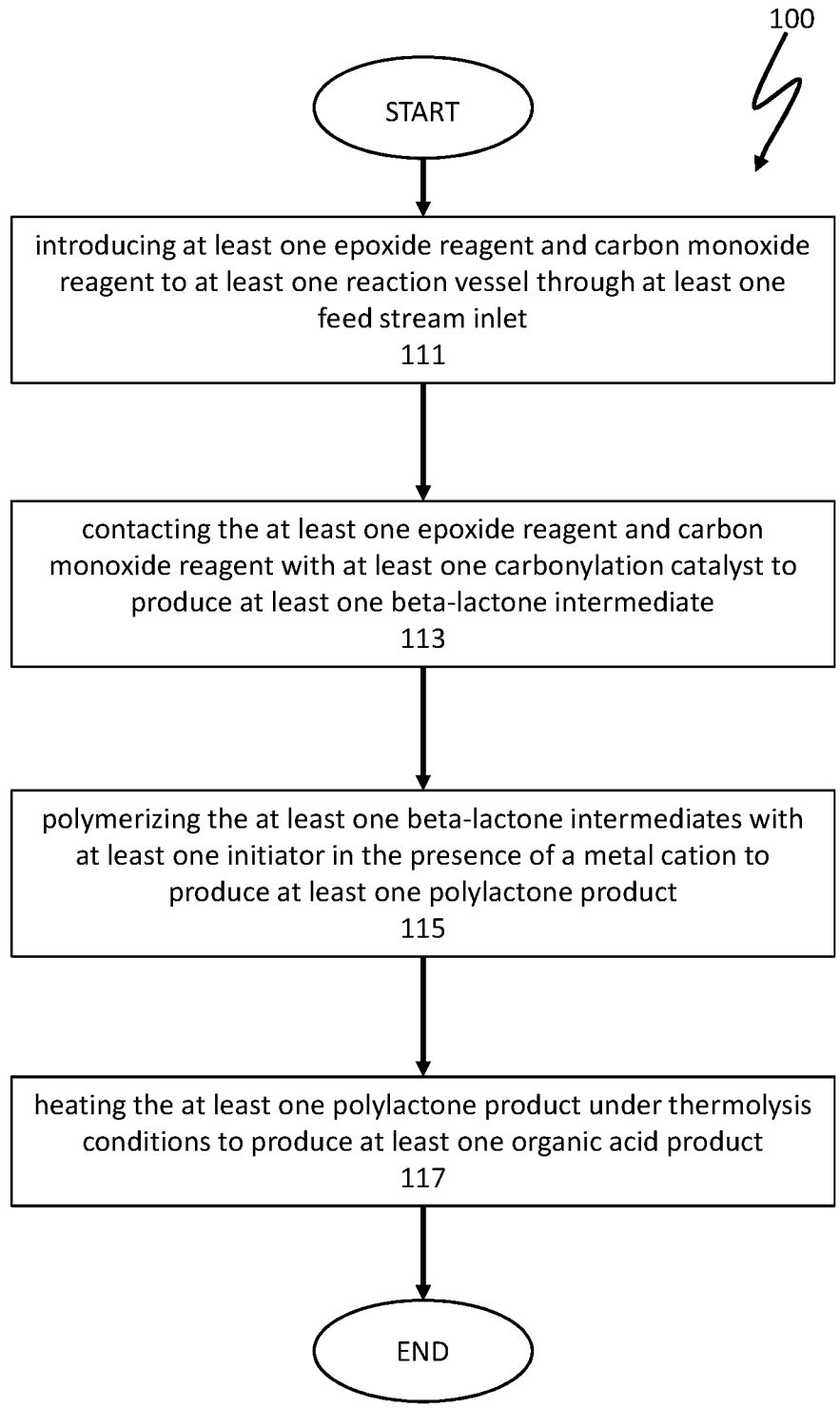
FIG. 1 illustrates steps of a preferred embodiment of a process for producing at least one organic acid product by thermolysis of at least one polylactone product.

The following description sets forth exemplary processes, parameters and the like. It should be recognized, however, that such description is not intended as a limitation on the scope of the present disclosure but is instead provided as a description of exemplary aspects.

Definitions

The terms bio-content and bio-based content mean biogenic carbon also known as bio-mass derived carbon, carbon waste streams, and carbon from municipal solid waste. In some variations, bio-content (also referred to as "bio-based content") can be determined based on the following:

Bio-content or Bio-based content=[Bio (Organic) Carbon]/[Total (Organic) Carbon] 100%, as determined by ASTM D6866 (Standard Test Methods for Determining the Bio-based (biogenic) Content of Solid, Liquid, and Gaseous Samples Using Radiocarbon Analysis).

The bio-content of the organic acids produced by thermolysis of the at least one polylactone product may depend based on the bio-content of the at least one epoxide reagent and at least one carbon monoxide reagent. For example, in some variations of the processes described herein, the at least one epoxide reagent and at least one carbon monoxide reagent described herein may have a bio-content of greater than 0%, and less than 100%. In certain variations of the processes described herein, the at least one epoxide reagent and at least one carbon monoxide reagent described herein may have a bio-content of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%. In certain variations, at least one epoxide reagent and at least one carbon monoxide reagent derived from renewable sources may be used. In other variations, at least a portion of the at least one epoxide reagent and/or at least one carbon monoxide reagent is derived from renewable sources.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^{rd}$ Edition, Cambridge University Press, Cambridge, 1987; the entire contents of each of which are incorporated herein by reference.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain at least one units of unsaturation, but which is not aromatic. Unless otherwise specified, aliphatic groups contain 1-30 carbon atoms. In some aspects, aliphatic groups contain 1-12 carbon atoms. In some aspects, aliphatic groups contain 1-8 carbon atoms. In some aspects, aliphatic groups contain 1-6 carbon atoms. In some aspects, aliphatic groups contain 1-5 carbon atoms, in some aspects, aliphatic groups contain 1-4 carbon atoms, in yet other aspects aliphatic groups contain 1-3 carbon atoms, and in yet other aspects, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein at least one carbon atoms are independently replaced by at least one atoms selected from the group consisting of oxygen, sulfur, nitrogen, phosphorus, or boron. In some aspects, one or two carbon atoms are independently replaced by at least one of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetitions of units derived, actually or conceptually, from molecules of low relative molecular mass. In some aspects, a polymer is comprised of only one monomer species. In some aspects, a polymer is a copolymer, terpolymer, heteropolymer, block copolymer, or tapered heteropolymer of at least one epoxides.

The term "unsaturated", as used herein, means that a moiety has at least one double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some aspects, the cycloalkyl has 3-6 carbons. Representative carbocyles include cyclopropane, cyclobutane, cyclopentane, cyclohexane, bicyclo[2,2,1]heptane, norbornene, phenyl, cyclohexene, naphthalene, and spiro[4.5]decane. The terms "cycloaliphatic", "carbocycle" or "carbocyclic" also include aliphatic rings that are fused to at least one aromatic or nonaromatic rings, such as decahydronaphthyl or tetrahydronaphthyl, where the radical or point of attachment is on the aliphatic ring. In some aspects, a carbocyclic group is bicyclic. In some aspects, a carbocyclic group is tricyclic. In some aspects, a carbocyclic group is polycyclic.

The term "alkyl," as used herein, refers to saturated, straight—or branched—chain hydrocarbon radicals derived from an aliphatic moiety containing between one and six carbon atoms by removal of a single hydrogen atom. Unless otherwise specified, alkyl groups contain 1-12 carbon atoms. In some aspects, alkyl groups contain 1-8 carbon atoms. In some aspects, alkyl groups contain 1-6 carbon atoms. In some aspects, alkyl groups contain 1-5 carbon atoms, in some aspects, alkyl groups contain 1-4 carbon atoms, in yet other aspects, alkyl groups contain 1-3 carbon atoms, and in yet other aspects alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some aspects, "aryl" refers to an aromatic ring system which includes, but is not limited to, phenyl, naphthyl, anthracyl and the like, which may bear at least one substituents. Also included within the scope of the term "aryl", as it is used herein, is a group in which an aromatic ring is fused to at least one additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to at least one aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, at least one, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to at least one aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic.

The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds may contain "optionally substituted" moieties. In general, the term "substituted", whether preceded by the term "optionally" or not, means that at least one hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned may include those that result in the formation of stable or chemically feasible compounds. The term "stable", as used herein, refers to compounds that are not substantially altered when subjected to conditions to allow for their production, detection, and, in some aspects, their recovery, purification, and use for at least one of the purposes disclosed herein.

In some chemical structures herein, substituents are shown attached to a bond which crosses a bond in a ring of the depicted molecule. This means that at least one of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

As used herein, the term "catalyst" refers to a substance the presence of which increases the rate of a chemical reaction, while not being consumed or undergoing a permanent chemical change itself.

Renewable sources means a source of carbon and/or hydrogen obtained from biological life forms that can replenish itself in less than one hundred years.

Renewable carbon means carbon obtained from biological life forms that can replenish itself in less than one hundred years.

Recycled sources mean carbon and/or hydrogen recovered from a previous use in a manufactured article.

Recycled carbon means carbon recovered from a previous use in a manufactured article.

As used herein, the term "about" preceding at least one numerical values means the numerical value±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

EXEMPLARY EMBODIMENTS OF THE INVENTION

In preferred embodiments of the present invention, the reactor systems and processes may produce at least one organic acid product by thermolysis of at least one polylactone product. One exemplary embodiment produces a highly pure organic acid product is as follows:

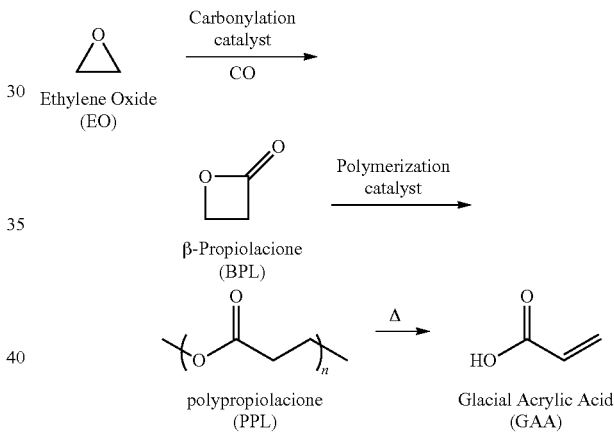

FIG. 1 illustrates a preferred embodiment of the present invention directed to producing at least one organic acid product comprising the following steps: introducing at least one epoxide reagent and at least one carbon monoxide reagent to at least one reaction vessel through at least one feed stream inlet 111; contacting the at least one epoxide reagent and at least one carbon monoxide reagent with at least one carbonylation catalyst to produce at least one beta-lactone intermediate 113; polymerizing the at least one beta-lactone intermediate with at least one initiator in the presence of a metal cation to produce at least one polylactone product 115; heating the at least one polylactone product under thermolysis conditions to produce at least one organic acid product 117. Advantageously, the processes of the present invention may control the presence of contaminates, impurities, catalytic materials, and/or reagents to provide for highly pure organic acid products.

In certain preferred embodiments of the present invention, the processes include a step for introducing at least one epoxide reagent and at least one carbon monoxide reagent to at least one reaction vessel through at least one feed stream inlet. In some embodiments, the at least one epoxide reagent and at least one carbon monoxide reagent may enter the at least one reaction vessel with mechanical assistance and/or by natural forces. In some embodiments, at least one mechanical pump may assist in introducing the at least one epoxide reagent and at least one carbon monoxide reagent to the at least one reaction vessel through the at least one feed stream inlet. In some embodiments, the at least one epoxide reagent and at least one carbon monoxide reagent may be stored at a higher atmospheric pressure than the at least one reaction vessel so that the at least one epoxides reagent and at least one carbon monoxide reagent may enter the at least one reaction vessel by the natural force of equalizing pressure.

In certain preferred embodiments, the processes of the present invention may include at least one epoxide reagent and at least one carbon monoxide reagent introduced to at least one reaction vessel at an amount sufficient for carbonylation under superatmospheric pressure. In certain embodiments, the at least one epoxide reagent and/or at least one carbon monoxide reagent is provided at a pressure in the range from about 50 psi (350 kPa) to about 5000 psi (35 MPa). In certain embodiments, the at least one epoxide reagent and/or at least one carbon monoxide reagent is provided at a pressure from about 50 psi (350 kPa) to about 1000 psi (7 MPa). In certain embodiments, the at least one epoxide reagent and/or at least one carbon monoxide reagent is provided at a pressure from about 50 psi (350 kPa) to about 500 psi (3.5 MPa). In certain embodiments, the at least one epoxide reagent and/or at least one carbon monoxide reagent is provided at a pressure from about 100 psi (700 kPa) to about 400 psi (2.8 MPa). In certain embodiments, the at least one epoxide reagent and/or at least one carbon monoxide reagent is provided at a pressure of about 200 psi (1.4 MPa).

In some embodiments, the processes of the present invention may introduce the at least one epoxide reagent and/or at least one carbon monoxide reagent at a rate of at least about 1000 kg/hr, at least about 1500 kg/hr, at least about 2000 kg/hr, at least about 5000 kg/hr, at least about 10000 kg/hr, or at least about 16000 kg/hr. In some embodiments, the processes of the present invention may introduce the at least one epoxide reagent and/or at least one carbon monoxide reagent at a rate of at least about 30 kmol/hr, at least about 40 kmol/hr, at least about 50 kmol/hr, or at least about 60 kg/hr.

In some embodiments, the processes of the present invention may introduce at least one epoxide reagent and/or at least one carbon monoxide reagent at a rate of about 1000 kg/hr to about 16000 kg/hr, or about 6000 kg/hr to about 16000 kg/hr. In some embodiments, the processes of the present invention may introduce the at least one epoxide reagent and/or at least one carbon monoxide reagent at a rate of at least about 30 kmol/hr, at least about 50 kmol/hr, at least about 200 kmol/hr, or at least about 600 kg/hr. In some embodiments, the processes of the present invention may introduce the at least one epoxide reagent and/or at least one carbon monoxide reagent at a rate of about 30 kmol/hr to about 60 kmol/hr, about 30 kmol/hr to about 600 kmol/hr, or about 200 kmol/hr to about 600 kmol/hr. In some embodiments, the flow rate from the at least one epoxide reagent and/or at least one carbon monoxide reagent is set to about the stoichiometric value for a carbonylation reaction, to about 5% higher than the stoichiometric value, to about 10% higher than the stoichiometric value, to about 15% higher than the stoichiometric value, or to about 20% higher than the stoichiometric value. Within the at least one reaction vessel, the at least one epoxide reagent and carbon monoxide reagent may contact at least one carbonylation catalyst to produce at least one beta-lactone intermediate, as generally depicted in the reaction scheme below:

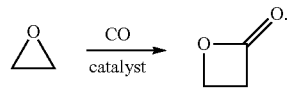

Carbonylation may utilize a metal carbonyl-Lewis acid catalyst such as those described in U.S. Pat. No. 6,852,865. In other aspects, the carbonylation step is performed with at least one of the carbonylation catalysts disclosed in U.S. patent application Ser. Nos. 10/820,958; and 10/586,826. In other aspects, the carbonylation step is performed with at least one of the catalysts disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In certain embodiments, the at least one carbonylation catalyst may be fed to the at least one reaction vessel in a manner similar to the at least one epoxide reagent and/or at least one carbon monoxide reagent. The at least one carbonylation catalyst can be pumped under carbon monoxide pressure to help ensure stability of the catalyst and can be cooled, optionally along with the feed, below ambient temperature to ensure stability. The at least one carbonylation catalyst can be introduced to the carbonylation chamber as either solids, that may be blanketed under carbon monoxide or a suitable inert gas, or in solution of solvent such as hexane or tetrahydrofuran.

In certain preferred embodiments, the step for contacting the at least one epoxide reagents and carbon monoxide reagents with the at least one carbonylation catalyst includes a metal carbonyl compound. Typically, a single metal carbonyl compound is provided, but in some embodiments, mixtures of two or more metal carbonyl compounds are provided. Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with at least one metal carbonyl compound. Preferably, the provided metal carbonyl compound is capable of ring-opening an epoxide and facilitating the insertion of carbon monoxide into the resulting metal carbon bond.

In some embodiments, a carbonylation catalyst comprising a metal carbonyl compound comprises an anionic metal carbonyl moiety. In other embodiments, a carbonylation catalyst comprising a metal carbonyl compound comprises a neutral metal carbonyl compound. In still other embodiments, a metal carbonyl compound comprises a metal carbonyl hydride or a hydrido metal carbonyl compound.

In some embodiments, a carbonylation catalyst comprising a metal carbonyl compound further comprises an anionic metal carbonyl species. The anionic metal carbonyl species may have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, a carbonylation catalyst comprising an anionic metal carbonyl species include a monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In some embodiments, the anionic metal carbonyl comprises $[Co(CO)_4]^-$. In some embodiments, a mixture of two or more anionic metal carbonyl complexes may be present in the carbonylation catalysts used in reactor systems and processes of the present invention.

In embodiments where the provided metal carbonyl compound is an anionic species, one or more cations must also necessarily be present. In some variations, no particular constraints on the identity of such cations. In some embodiments, the cation associated with an anionic metal carbonyl compound comprises a reaction component of another category described herein. For example, in some embodiments, the metal carbonyl anion is associated with a cationic Lewis acid. In other embodiments, a cation associated with a provided anionic metal carbonyl compound is a simple metal cation such as those from Groups 1 or 2 of the periodic table (e.g., $Na^+$, $Li^+$, $K^+$, $Mg^{2+}$ and the like). In other embodiments, a cation associated with a provided anionic metal carbonyl compound is a bulky non-electrophilic cation such as an 'onium salt' (e.g., $Bu_{4N}^+$, $PPN^+$, $Ph_4P^+$ $Ph_4As^+$, and the like). In other embodiments, a metal carbonyl anion is associated with a protonated nitrogen compound (e.g., a cation may comprise a compound such as MeTBD-H$^+$, DMAP-H$^+$, DABCO-H$^+$, DBU-H$^+$ and the like). In some embodiments, compounds comprising such protonated nitrogen compounds are provided as the reaction product between an acidic hydrido metal carbonyl compound and a basic nitrogen-containing compound (e.g., a mixture of DBU and $HCo(CO)_4$).

In certain preferred embodiments, a carbonylation catalyst utilized in the reactor systems and processes described herein comprises a neutral metal carbonyl compound. In some embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula $QM'(CO)_{w'}$. In some embodiments, the neutral metal carbonyl has the general formula $M'(CO)_{w'}$. In some embodiments, the neutral metal carbonyl has the general formula $QM'_2(CO)_{w'}$. In some embodiments, the neutral metal carbonyl has the general formula $M'_2(CO)_{w'}$. Suitable neutral metal carbonyl compounds include, but are not limited to: $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5Ru_3(CO)_{12}$, $Os_3(CO)_{12}Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, and $Ni(CO)_4$.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the carbonylation catalyst utilized in the reactor systems and processes described above further includes a Lewis acidic component. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, a carbonylation catalyst including Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., $R_2BX$), a dihalo monoalkyl compound (e.g., $RBX_2$), an aryl halo boron compound (e.g., $Ar_2BX$ or $ArBX_2$), or a trihalo boron compound (e.g., $BCl_3$ or $BBr_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where carbonylation catalysts used in the reactor systems and processes of the present invention include a cationic metal complex, the metal complex has the formula $[(L^c)_vM_b]^{z+}$, where:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

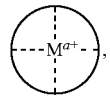
I wherein:

is a multidentate ligand;
M is a metal atom coordinated to the multidentate ligand;
a is the charge of the metal atom and ranges from 0 to 2.

In some embodiments, provided metal complexes conform to structure II:

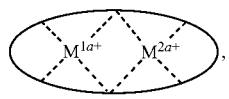
II where:
a is as defined above (each a may be the same or different), and
$M^1$ is a first metal atom;
$M^2$ is a second metal atom;

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In some embodiments, the multidentate ligand is a salen derivative. In other embodiments, the multidentate ligand is a porphyrin derivative.

In other embodiments, the multidentate ligand is a tetraphenylporphyrin derivative. In other embodiments, the multidentate ligand is a corrole derivative.

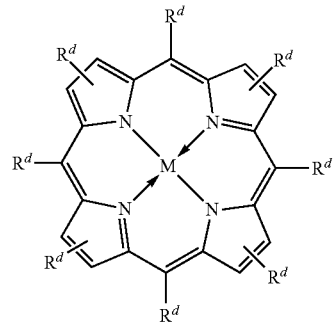
1

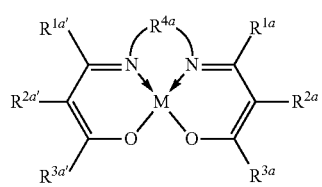
2

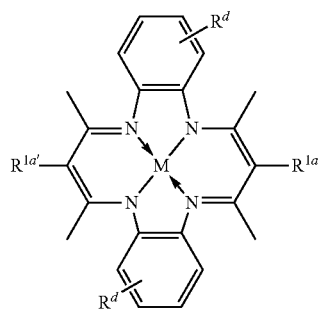
3

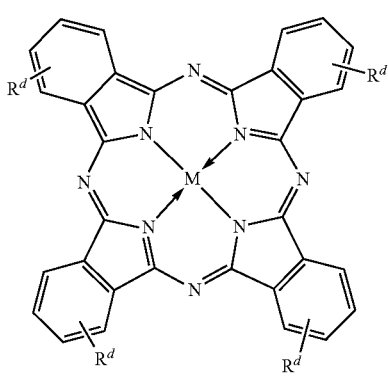
4

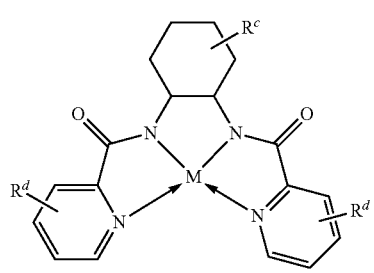
5

-continued

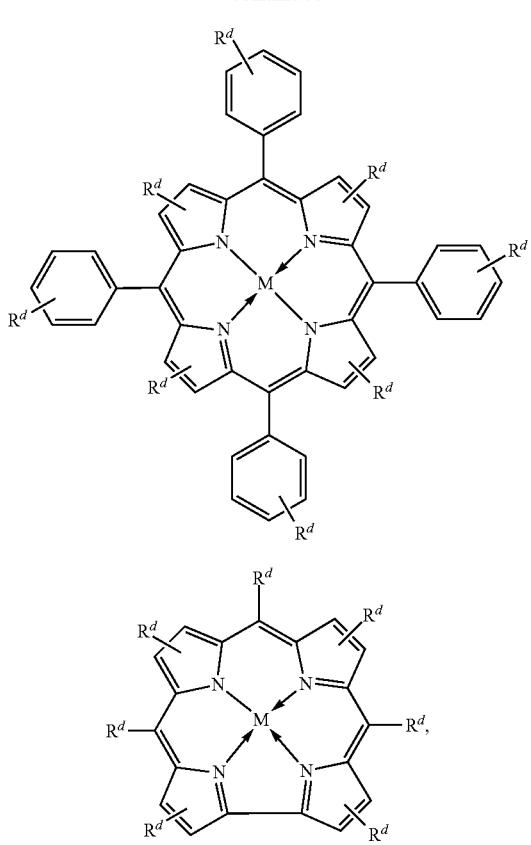

where each of $R^c$, $R^d$, $R^{1a}$, $R^{2a}$, $R^{3a}$, $R^{4a}$, $R^{1a'}$, $R^{2a'}$, $R^{3a'}$, and M, is as defined and described in the classes and subclasses herein.

In some embodiments, Lewis acids provided carbonylation catalysts used in reactor systems and processes described herein comprise metal-porphinato complexes.

In some embodiments, the moiety

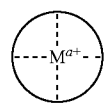

has the structure:

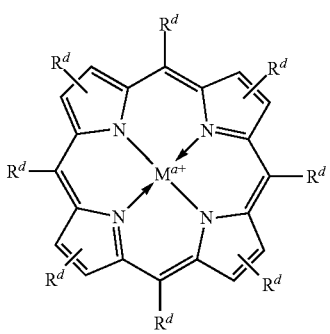

where each of M and a is as defined above and described in the classes and subclasses herein, and $R^d$ at each occurrence is independently hydrogen, halogen, —$OR^4$, —$NR^y{}_2$, —$SR^y$, —CN, —$NO_2$, —$SO_2R^y$, —$SOR^y$, —$SO_2NR^y{}_2$; —CNO, —$NR^ySO_2R^y$, —NCO, —$N_3$, —$SiR^y{}_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or $R^y$.

In some embodiments, the moiety

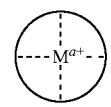

has the structure:

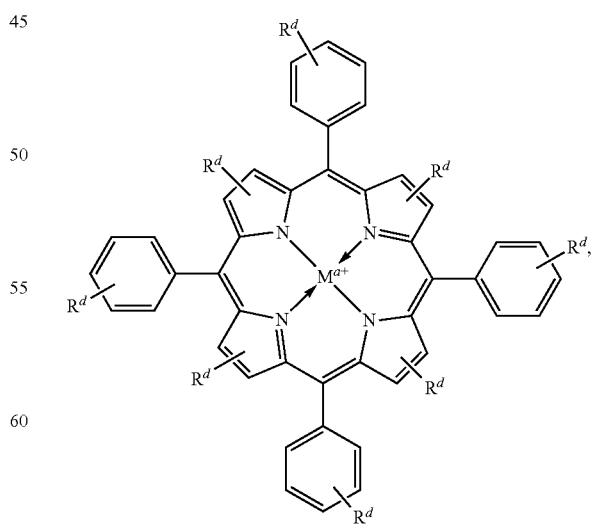

where M, a and $R^d$ are as defined above and in the classes and subclasses herein.

In some embodiments, the moiety

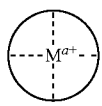

has the structure:

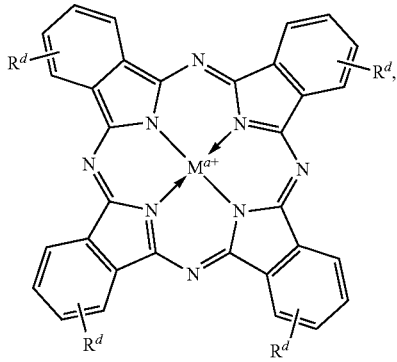

where M, a and $R^d$ are as defined above and in the classes and subclasses herein.

In some embodiments, Lewis acids included in carbonylation catalysts used in reactor systems and processes described herein comprise metallo salenate complexes.

In some embodiments, the moiety

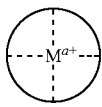

has the structure:

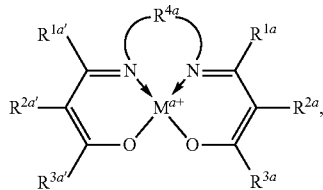

wherein:

M, and a are as defined above and in the classes and subclasses herein, $R^{1a}$, $R^{1a'}$, $R^{2a}$, $R^{2a'}$, $R^{3a}$, and $R^{3a'}$ are independently hydrogen, halogen, —$OR_4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and $R^{4a}$ is selected from the group consisting of:

e)

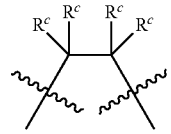

f)

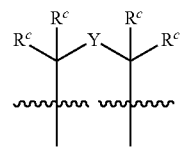

g)

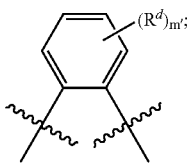

and
h)

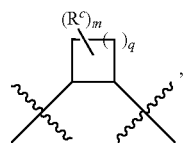

where $R^c$ at each occurrence is independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:

two or more $R^c$ groups may be taken together with the carbon atoms to which they are attached and any intervening atoms to form one or more rings;

when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

where $R^4$ and $R^y$ are as defined above and in classes and subclasses herein;

Y is a divalent linker selected from the group consisting of: —$NR^y$—, —$N(R^{y})C(O)$—, —$C(O)NR^y$—, —O—, —C(O)—, —OC(O)—, —C(O)O—, —S—, —SO—, —$SO_2$—, —C(=S)—, —C(=$NR^y$)—, —N=N—; a polyether; a $C_3$ to $C_8$ substituted or unsubstituted carbocycle; and a $C_1$ to $C_8$ substituted or unsubstituted heterocycle;

m' is 0 or an integer from 1 to 4, inclusive;

q is 0 or an integer from 1 to 4, inclusive; and x is 0, 1, or 2.

In some embodiments, a provided Lewis acid comprises a metallo salen compound, as shown in formula Ia:

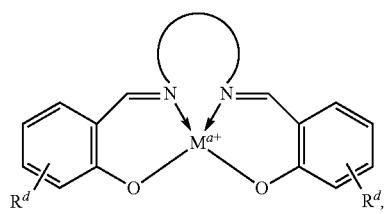

Ia wherein each of M, $R^d$, and a, is as defined above and in the classes and subclasses herein, ⌒ represents is an optionally substituted moiety linking the two nitrogen atoms of the diamine portion of the salen ligand, where ⌒ is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —$NR^y$—, —$N(R^{y})C(O)$—, —$C(O)N(R^y)$—, —$OC(O)N(R^y)$—, —$N(R^y)C(O)O$—, —OC(O)O—, —O—, —C(O)—, —OC(O)—, —C(O)O—, —S—, —SO—, —$SO_2$—, —C(=S)—, —C(=$NR^y$)—, —C(=$NOR^y$)— or —N=N—.

In some embodiments metal complexes having formula Ia above, at least one of the phenyl rings comprising the salicylaldehyde-derived portion of the metal complex is independently selected from the group consisting of:

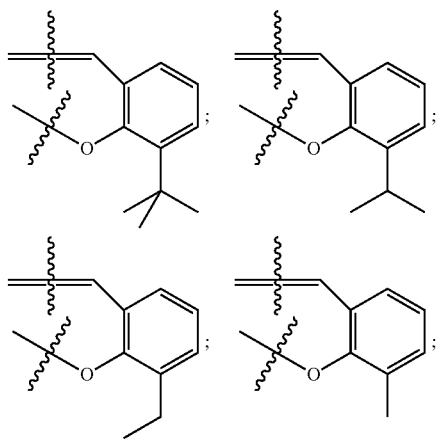

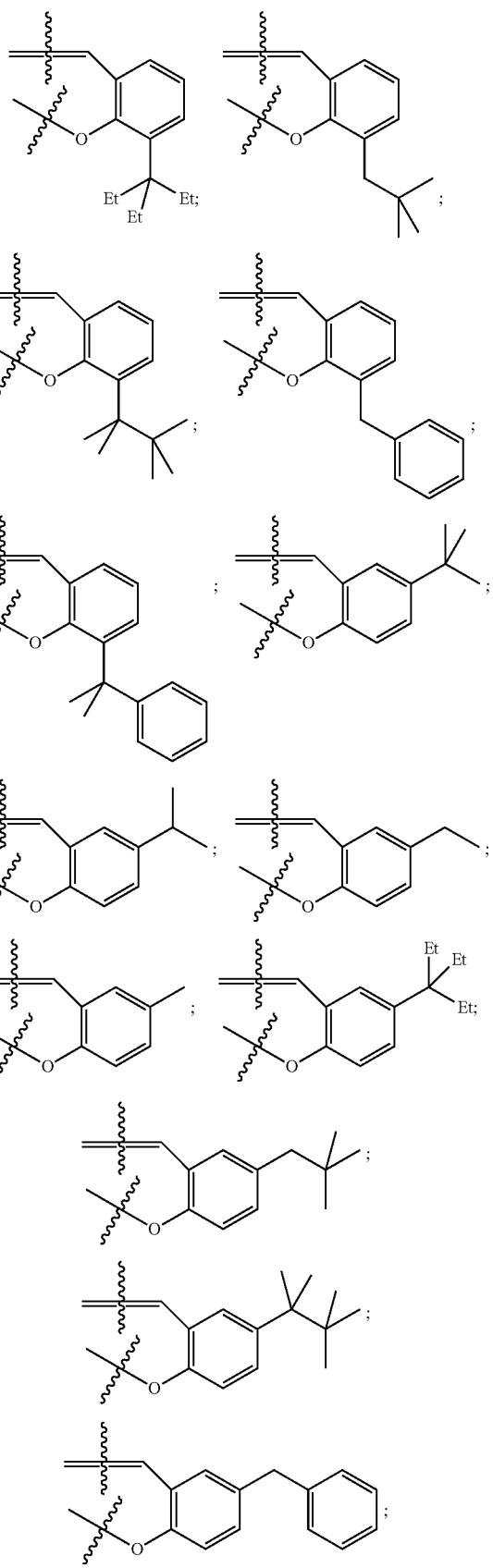

-continued

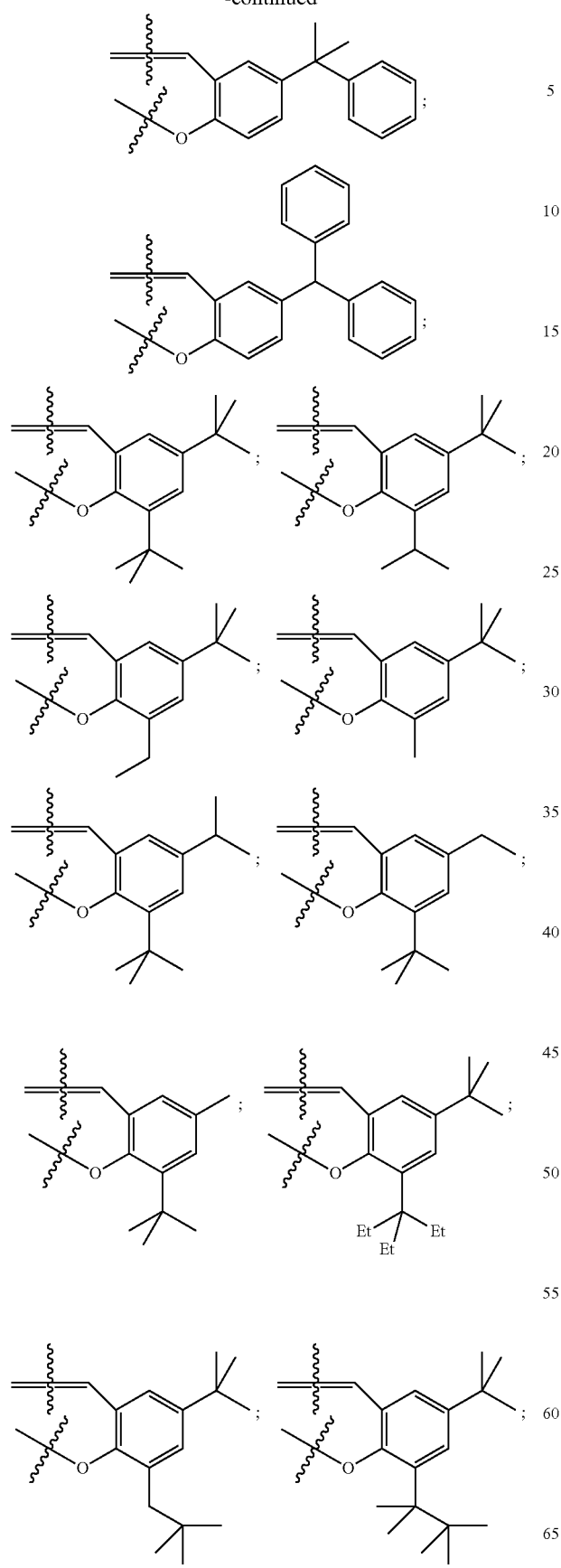

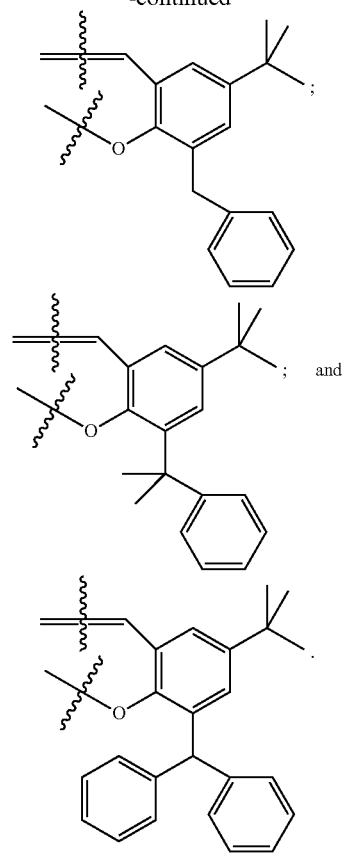

In some embodiments, a provided Lewis acid comprises a metallo salen compound, conforming to one of formulae Va or Vb:

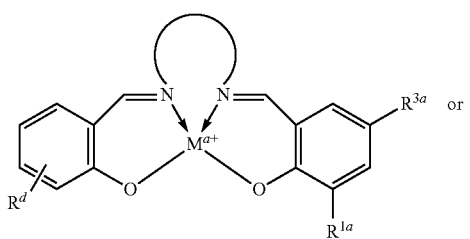
Va

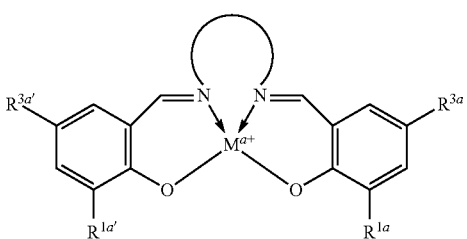
Vb where M, a, $R^d$, $R^{1a}$, $R^{3a}$, $R^{1a'}$, $R^{3a'}$, and ⌒, are as defined above and in the classes and subclasses herein.

In some embodiments of metal complexes having formulae Va or Vb, each $R^{1a}$ and $R^{3a}$ is, independently, optionally substituted $C_1$-$C_{20}$ aliphatic.

In some embodiments, the moiety ⌒ comprises an optionally substituted 1,2-phenyl moiety.

In some embodiments, Lewis acids included in carbonylation catalysts used in reactor systems and processes described herein comprise metal-tmtaa complexes. In some embodiments, the moiety

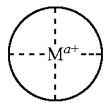

has the structure:

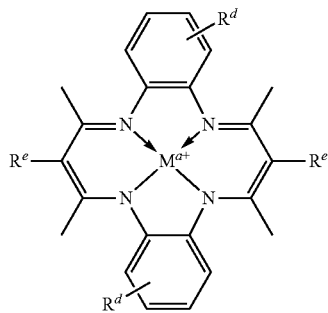

where M, a and $R^d$ are as defined above and in the classes and subclasses herein, and $R^e$ at each occurrence is independently hydrogen, halogen, —OR, —NR$^y$$_2$, —SR$^y$, —CN, —NO$_2$, —SO$_2$R$^y$, —SOR$^y$, —SO$_2$NR$^y$$_2$; —CNO, —NR$^y$SO$_2$R$^y$, —NCO, —N$_3$, —SiR$^y$$_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

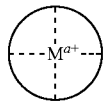

has the structure:

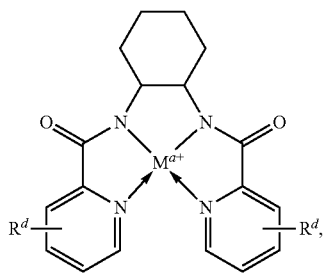

where each of M, a, $R^c$ and $R^d$ is as defined above and in the classes and subclasses herein.

In some embodiments, where carbonylation catalysts used in reactor systems and processes described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper.

In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ has an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the carbonylation catalyst includes a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand.

In some embodiments, the carbonylation catalyst includes a carbonyl cobaltate in combination with an aluminum porphyrin compound. In some embodiments, the carbonylation catalyst is [(TPP)Al(THF)$_2$][Co(CO)$_4$] where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M, $M^1$, or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

In certain embodiments, the carbonylation catalyst includes a carbonyl cobaltate in combination with an aluminum porphyrin compound. In certain embodiments, the carbonylation catalyst includes a carbonyl cobaltate in combination with a chromium porphyrin compound. In certain embodiments, the carbonylation catalyst includes a carbonyl cobaltate in combination with a chromium salen compound. In certain embodiments, the carbonylation catalyst includes a carbonyl cobaltate in combination with a chromium salophen compound. In certain embodiments, the carbonylation catalyst includes a carbonyl cobaltate in combination with an aluminum salen compound. In certain embodiments, the carbonylation catalyst includes a carbonyl cobaltate in combination with an aluminum salophen compound.

Table 1 illustrated below includes Column A directed to a non-exhaustive list of epoxides which may undergo carbonylation to produce at least one beta-lactone intermediate according to the processes of the present invention and Column B directed to a non-exhaustive list of beta-lactone intermediates which may undergo ring opening polymerization according to the processes of the present invention.

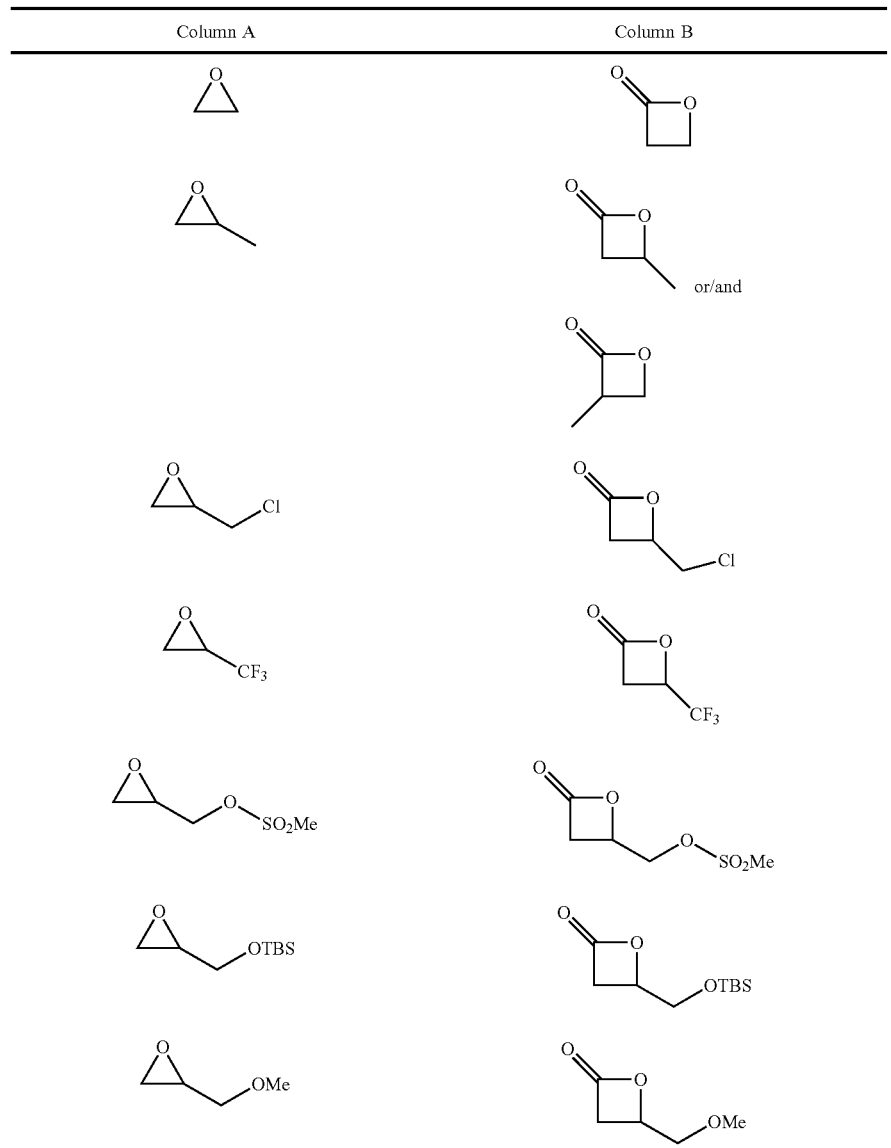

-continued
| Column A | Column B |
|---|---|
| 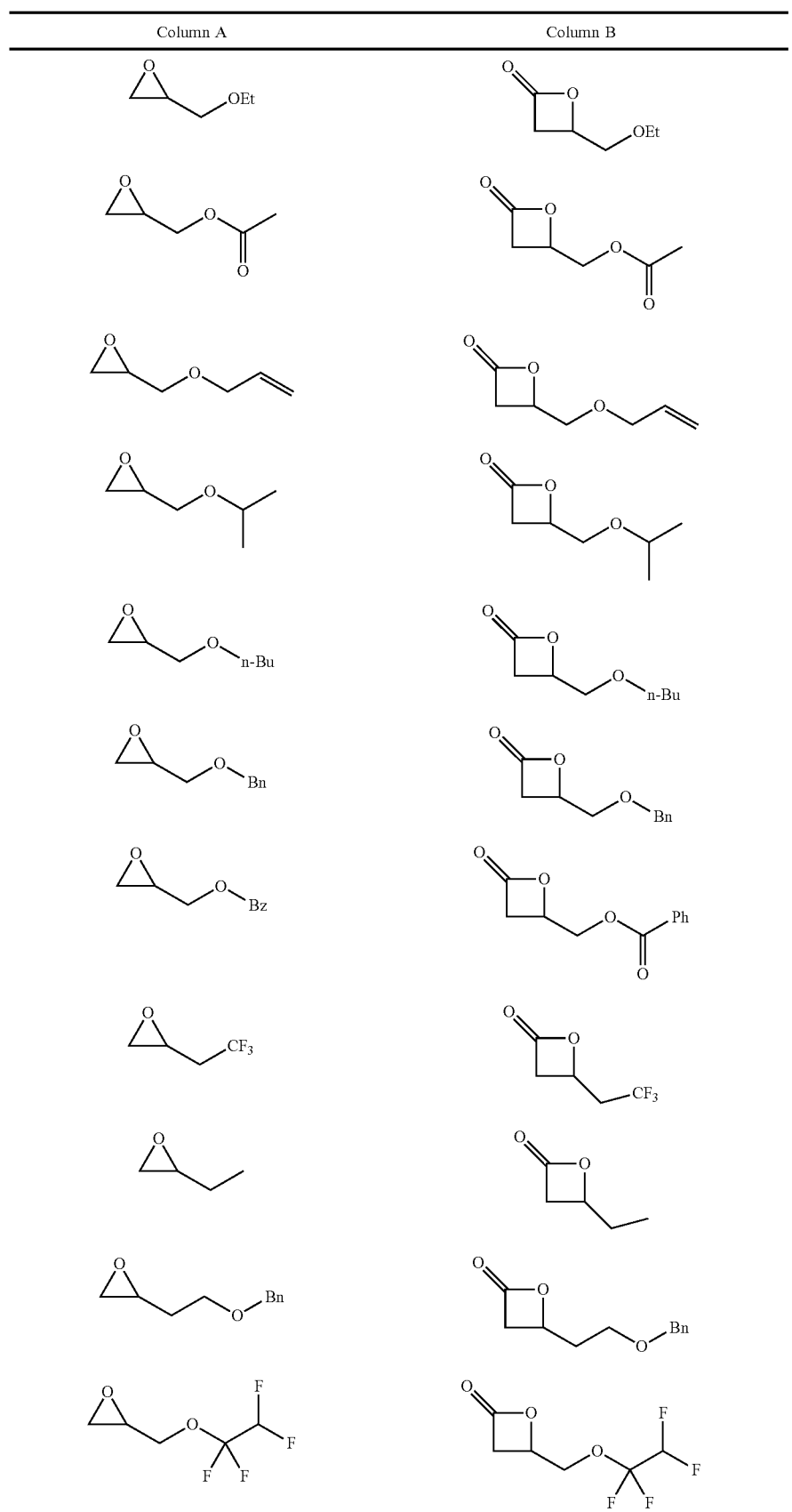 | |

-continued
| Column A | Column B |
|---|---|
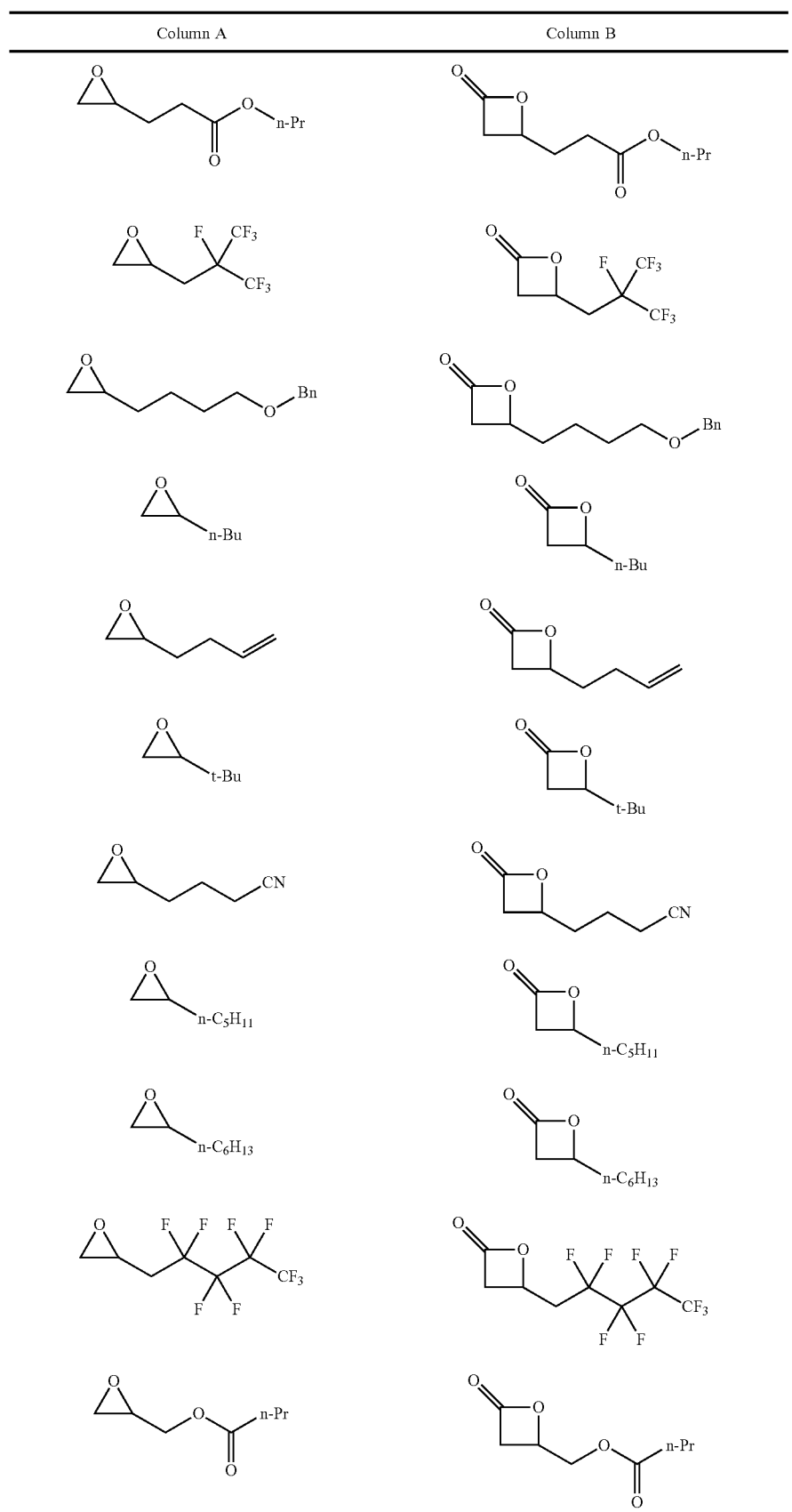

-continued
| Column A | Column B |
|---|---|
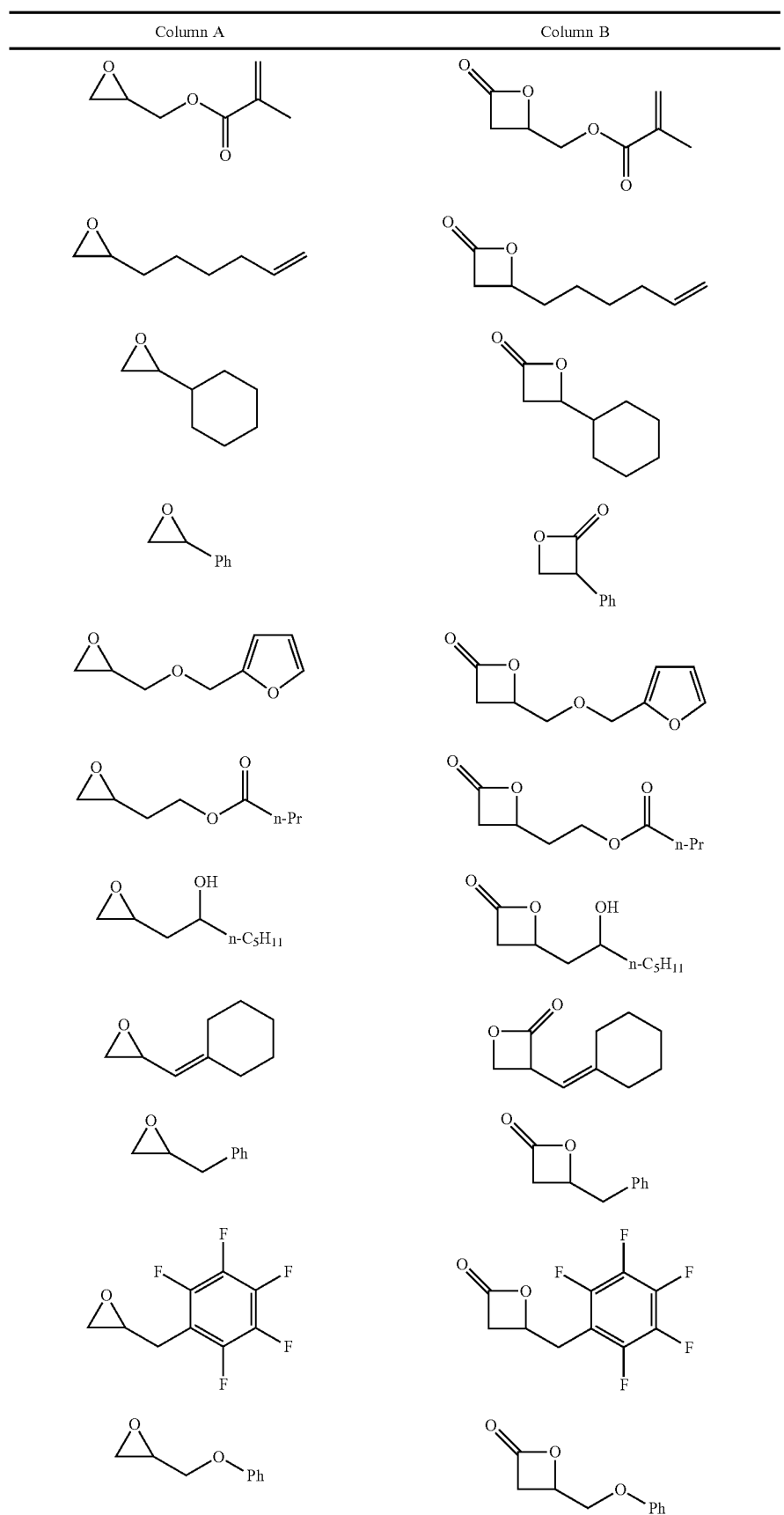

-continued
| Column A | Column B |
|---|---|
| 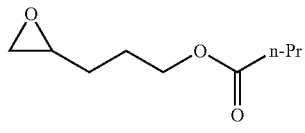 | 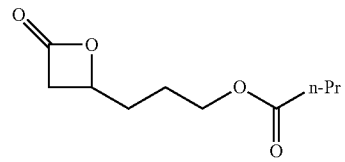 |
| 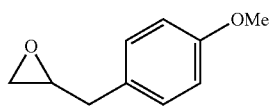 [SMILES: COc1ccc(CC2CO2)cc1] | 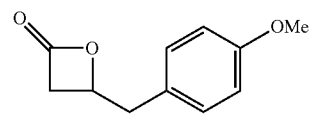 [SMILES: COc1ccc(CC2CC(=O)O2)cc1] |
| 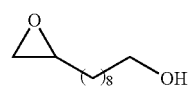 | 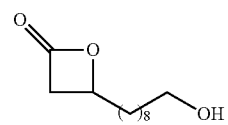 |
| 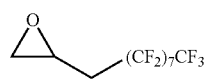 | 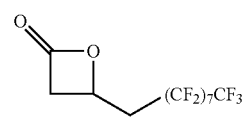 |
| 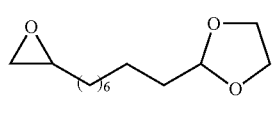 | 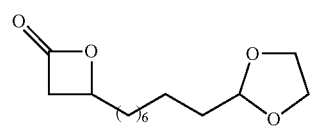 |
| 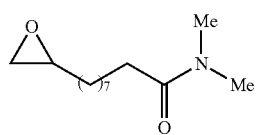 | 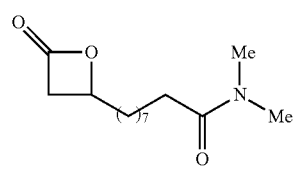 |
| 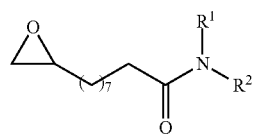 | 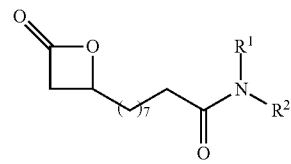 |
| 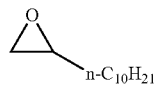 | 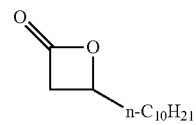 |
|  | 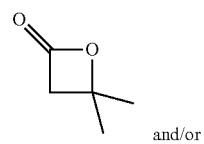 and/or 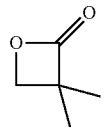 |

-continued
| Column A | Column B |
|---|---|
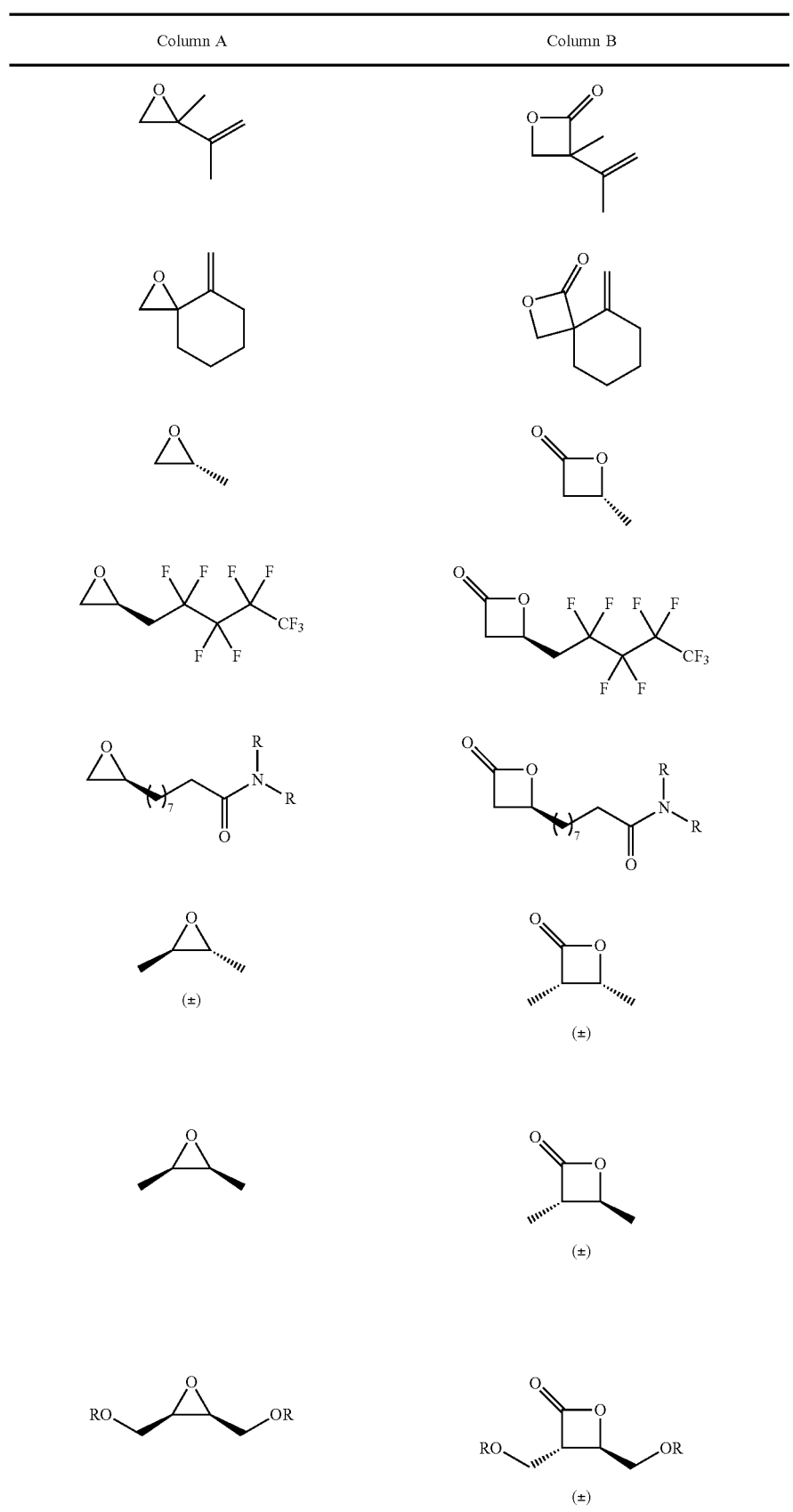

| Column A | Column B |
| --- | --- |
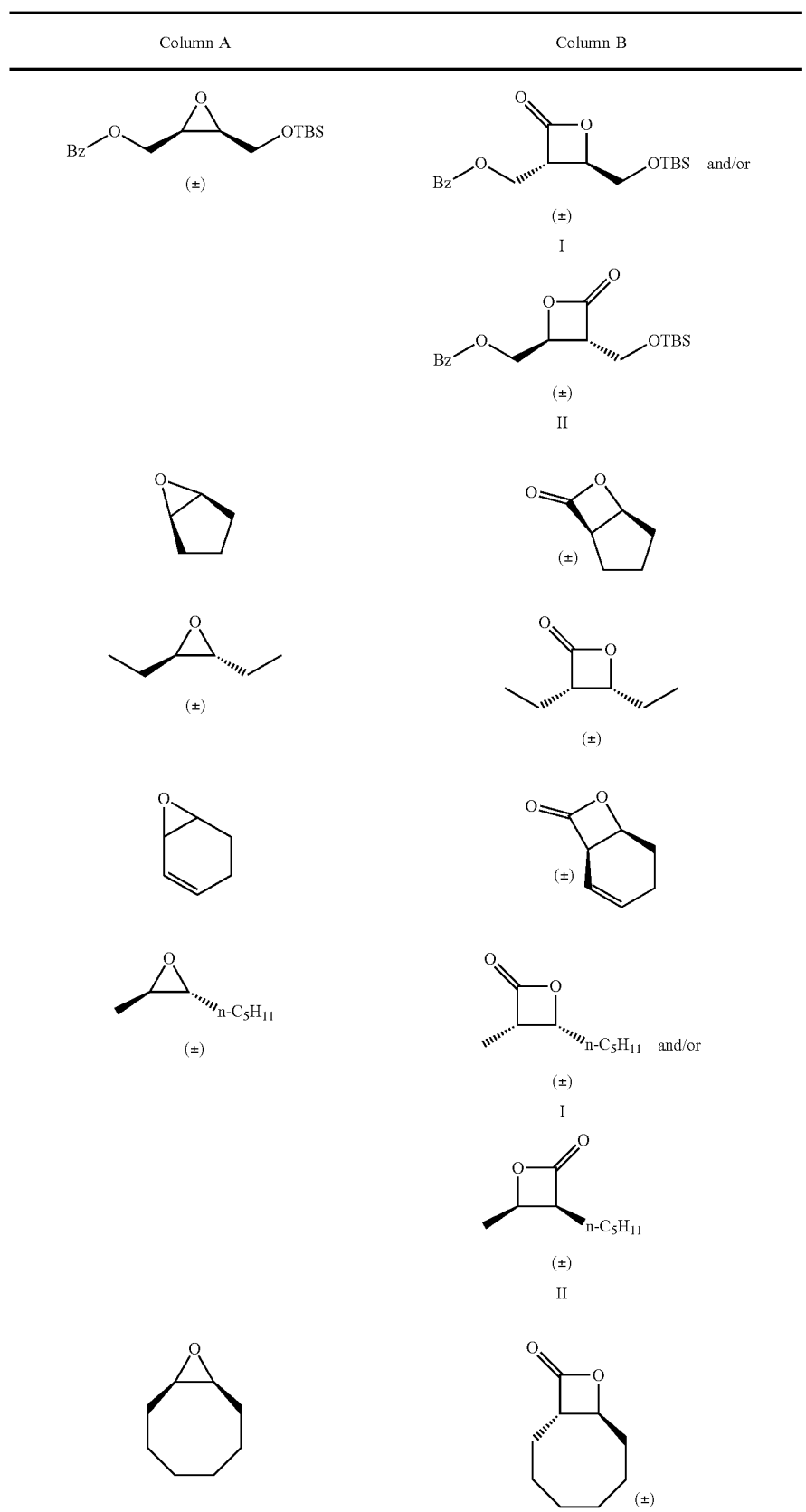

-continued
| Column A | Column B |
|---|---|
|  | 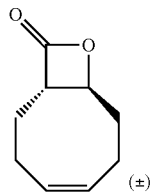 [SMILES: O=C1O[C@H]2CC/C=C\CC[C@H]12] (±) |
| 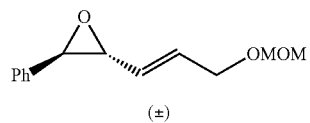 (±) | 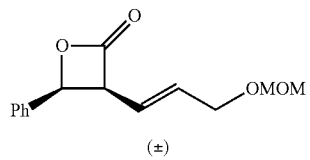 (±) |
| 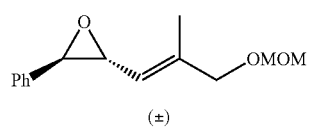 (±) | 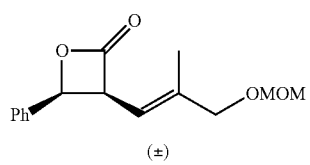 (±) |
| 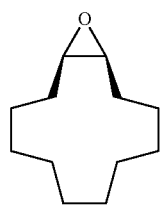 [SMILES: C1CCCCC[C@H]2O[C@H]2CCCC1] | 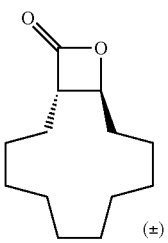 [SMILES: O=C1O[C@H]2CCCCCCCCCC[C@H]12] (±) |
| 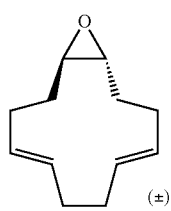 [SMILES: C1=C/CC[C@H]2O[C@@H]2CC/C=C/CC/1] (±) | 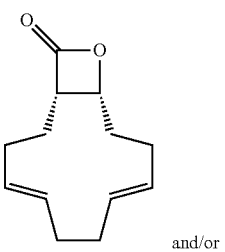 and/or 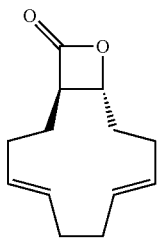 |
|  | 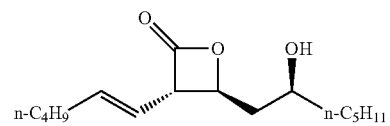 |

| Column A | Column B |
|---|---|

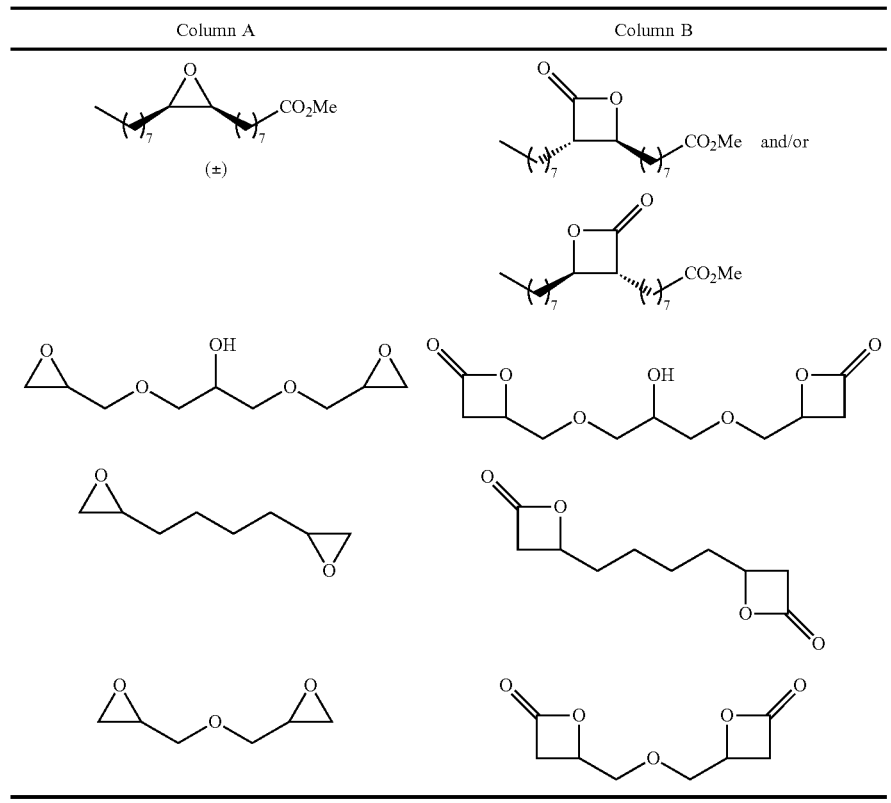

In certain preferred embodiments, the at least one polylactone is produced by ring opening polymerization of the at least one beta-propiolactone intermediate.

In preferred embodiments of the present invention, the processes of the present invention include a step for polymerizing the at least one beta-lactone intermediate with at least one polymerization initiator in the presence of at least one metal cation to produce at least one polylactone product. In certain embodiments of this invention, the polymerization initiator is an ionic initiator having the general formula of M"X where M" is cationic and X is anionic. The M" is selected from the group consisting of $Li^+$, $Na^+$, $K+$, $Mg^{2+}$, $Ca^{2+}$, and $Al^{3+}$. In some embodiments, M" is $Na^+$. In some embodiments, M" is an organic cation. In some embodiments, the organic cation is selected from the group consisting of quaternary ammonium, imidazolium, and bis(triphenylphosphine)iminium. In some embodiments, the quaternary ammonium cation is tetraalkyl ammonium.

The X is a nucleophilic anion such as, but not limited to, compounds comprising at least one carbonxylate group, at least one alkoxide group, at least one phenoxide group, and combination thereof. In some embodiments, the nucleophilic anion is selected from the group consisting of halides, hydroxide, alkoxide, carboxylate, and combination thereof. In some embodiments, the ionic initiator is sodium acrylate. In some embodiments, the ionic initiator is tetrabutylammonium acrylate. The suitable anionic nuclephiles include $R^xO^-$, $R^xC(=O)O^-$, $R^xS^-$, $R^xO(C=O)O^-$, halide (e.g., $Br^-$, $I^-$, $Cl^-$), $R^x(SO_2)O^-$ and $PR^x_3O^-$, wherein each $R^x$ is, independently, selected from hydrogen, optionally substituted aliphatic, optionally substituted heteroaliphatic, optionally substituted aryl and optionally substituted heteroaryl. In certain embodiments where the anionic nucleophile is $R^xC(=O)O^-$, $R^x$ is selected from optionally substituted aliphatic, fluorinated aliphatic, optionally substituted heteroaliphatic, optionally substituted aryl, fluorinated aryl, and optionally substituted heteroaryl. For example in certain aspects the initiator may be $CH_2=CHCO_2^-$, $CH_3CO_2^-$, or $CF_3CO_2^-$.

In certain embodiments, the homogeneous polymerization initiator is a quaternary ammonium salt (for example, tetrabutylammonium (TBA) acrylate, TBA acetate, trimethylphenylammonium acrylate, or trimethylphenylammonium acetate) or a phosphine (for example, tetraphenyl phosphonium acrylate). In some aspects, the catalyst is tetrabutylammonium acrylate, sodium acrylate, potassium acrylate, iron chloride, tetrabutylammonium acetate, trimethylphenylammonium acrylate, trimethylphenylammonium acetate, or tetraphenyl phosphonium acrylate.

The polymerization process may further comprise at least one polymerization initiator including but not limited to amines, polyamines, phosphines amongst others. Further, a variety of polymerization initiators may be used in the polymerization process, including by not limited to carbonates of alkali- and alkaline earth metals. In certain aspects, suitable polymerization initiators include carboxylate salts of metal ions or organic cations. In certain aspects, a polymerization initiator is combined with the production stream containing at least one beta-lactone intermediate. In certain aspects, the molar ratio of the polymerization initiator to the at least one beta-lactone intermediate is about 1:15000. In certain aspects, the molar ratio of polymerization intiator:beta-lactone intermediate is about 1:100, 1:10000, 1:1000, 1:20000 or a range including any two of these ratios.

The at least one polymerization initiator may comprise a carboxylate salt, the carboxylate has a structure such that upon initiating polymerization of at least one beta-lactone intermediate, the at least one polylactone chains produced have an acrylate chain end. In certain aspects, the carboxylate ion on a polymerization initiator is the anionic form of a chain transfer agent used in the polymerization process.

In certain embodiments, steps for polymerizing the at least one beta-lactone intermediate may be performed in the presence of a solvent. Suitable solvents for the polymerization with cyclic anhydride monomers include methylene chloride, chloroform, tetrahydrofuran, sulfolane, N-methyl pyrrolidone, diglyme, triglyme, tetraglyme, and dibasic esters.

In some embodiments, suitable catalysts, initiators, and solvent for the polymerization of the beta-lactone monomers can be found in U.S. Ser. No. 15/197,838 filed Jun. 30, 2016 the contents of which is herein incorporated by reference in its entirety. Other Catalysts suitable for the ring-opening polymerization step of the processes disclosed herein are disclosed, for example, in: Journal of the American Chemical Society (2002), 124(51), 15239-15248 Macromolecules, vol. 24, No. 20, pp. 5732-5733, Journal of Polymer Science, Part A-1, vol. 9, No. 10, pp. 2775-2787; Inoue, S., Y. Tomoi, T. Tsuruta & J. Furukawa; Macromolecules, vol. 26, No. 20, pp. 5533-5534; Macromolecules, vol. 23, No. 13, pp. 3206-3212; Polymer Preprints (1999), 40(1), 508-509; Macromolecules, vol. 21, No. 9, pp. 2657-2668; and Journal of Organometallic Chemistry, vol. 341, No. 1-3, pp. 83-9; and in U.S. Pat. Nos. 3,678,069, 3,169,945, 6,133,402; 5,648, 452; 6,316,590; 6,538,101; and 6,608,170. The entirety of each of which is hereby incorporated herein by reference.

In preferred embodiments, the processes of the present invention include a step for heating at least one polylactone product under thermolysis conditions to produce at least one organic acid product in at least one reaction vessel defining a thermolysis chamber. Under thermolysis conditions, the at least one polylactone product can generally be converted to organic acid according to the following scheme:

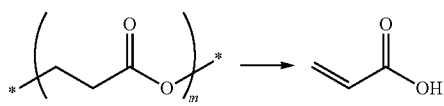

In certain embodiments, the at least one polylactone product may undergo thermolysis continuously (e.g. in a fed batch reactor or other continuous flow reactor format). In certain embodiments, the continuous thermolysis process is linked to a continuous polymerization process to provide at least one organic acid product at a rate matched to the consumption rate of the reactor.

In certain preferred embodiments of the present invention, the processes for heating the at least one polylactone product under thermolysis conditions to produce at least one organic acid product may favor β-elimination to produce at least one unsaturated alkenoic acid. Certain exemplary thermolysis reactions are shown below as non-limiting examples:

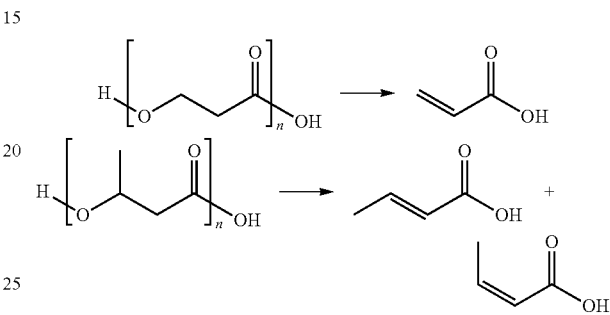

In certain embodiments of the present invention, the at least one epoxide reagents may include a diepoxide, for example, 1,2-butadiene diepoxide. Certain exemplary reactions for producing at least one organic acid product from a diepoxide are shown below as non-limiting examples:

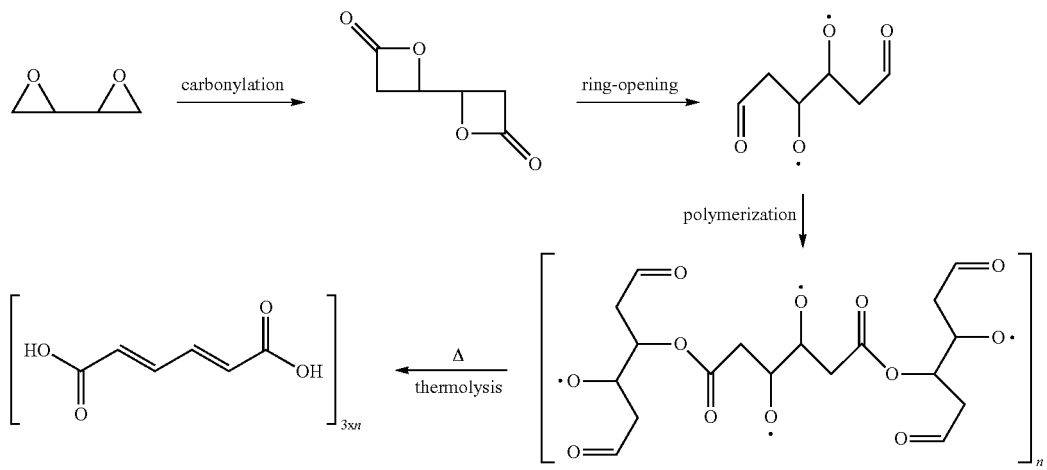

Figure 2:
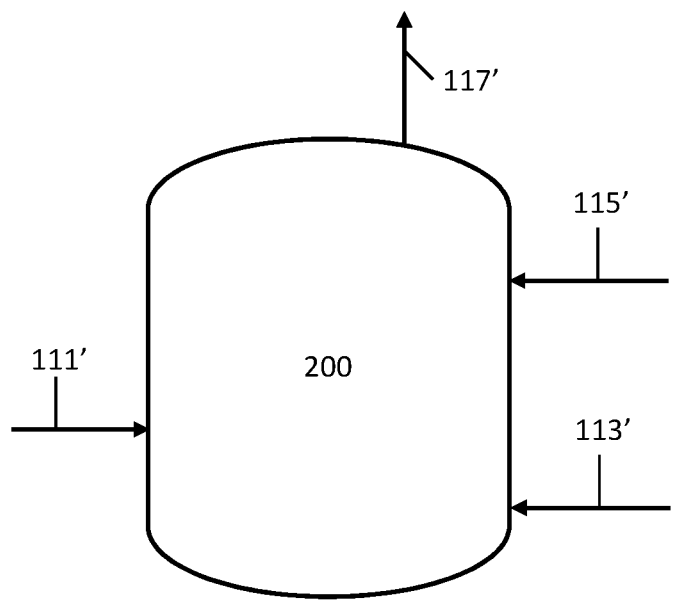
FIG. 2 is a schematic process flow diagram illustrating steps of the process flow from FIG. 1.

FIG. 2 provides a schematic view diagram of some of the process steps of FIG. 1. The process flow of FIG. 2 is configured for production of at least one organic acid product in at least one reaction vessel 200. At least one epoxide reagent and at least one carbon monoxide reagent may be introduced through at least one feed stream inlet defined by the at least one reaction vessel 111'. The at least one epoxide reagent and at least one carbon monoxide reagent may be contacted with at least one carbonylation catalyst to produce at least one beta-lactone intermediate such as by directing the at least one carbonylation catalysts through at least one feed stream inlet 113. The at least one beta-lactone intermediate may be polymerized such as by directing at least one initiator in the presence of a metal cation through at least one feed stream inlet to produce at least one polylactone product 115. Heat may be introduced to the reaction vessel 200 such as by a heating baffle for heating the at least one polylactone product under thermolysis conditions to produce at least one organic acid product 117.

Figure 3:
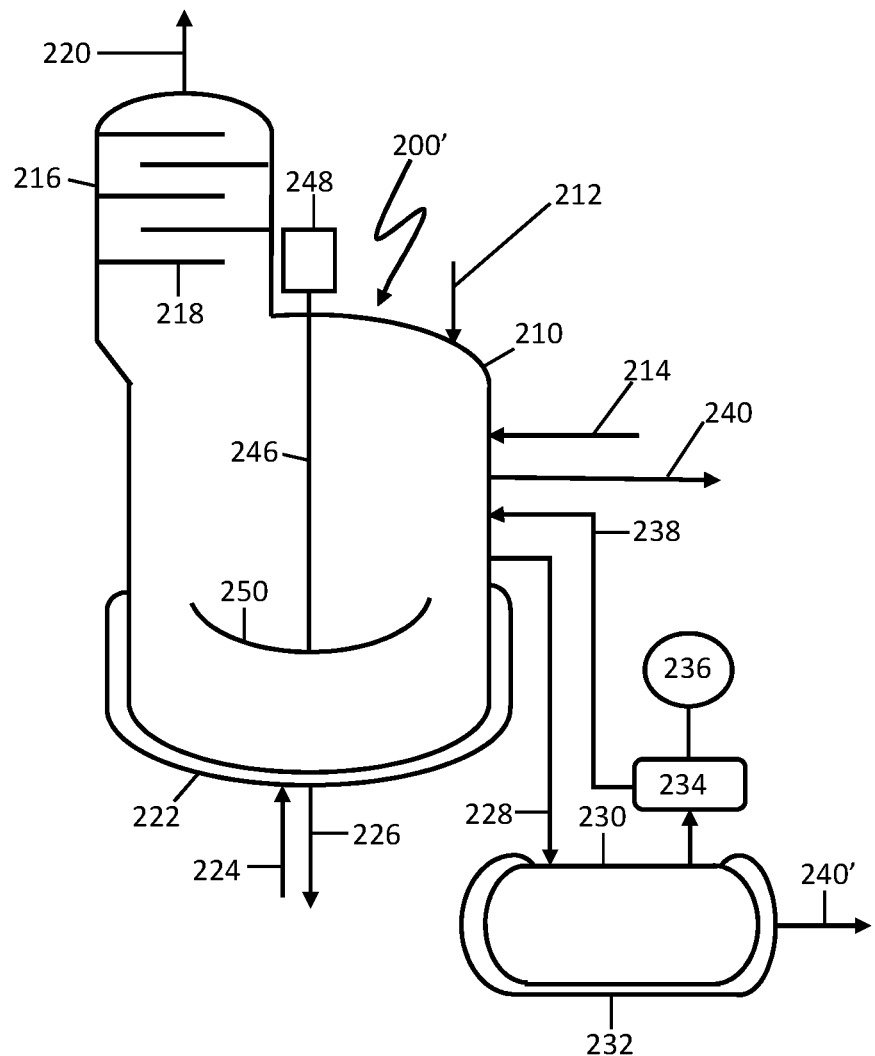
FIG. 3 schematically illustrates a preferred reaction vessel and related equipment in a process flow diagram for thermolysis.

FIG. 3 illustrates a preferred embodiment of a reaction vessel 200' configured for thermolysis. In the FIG. 3 illustrated embodiment, the reaction vessel 200' defines a thermolysis chamber 210 sized and shaped to define interior volume adapted for receiving a feed stream comprising at least one polylactone products and a retaining volume adapted for retaining the at least one polylactone products. The feed stream comprising the at least one polylactone products may be passed to the thermolysis chamber 210 by a feed stream inlet 212 defined by the thermolysis chamber 210. In some embodiments, a polymerization inhibitor may be directly introduced to the thermolysis chamber 210 by an additive stream inlet 214 defined by a portion of the thermolysis chamber 210. Additionally, oligomers of a variety of chain lengths, residual polymerization initiator, polymerization inhibitor, impurities, and/or other unwanted materials may be removed directly from the thermolysis chamber 210 by a purge stream outlet 240 defined by the thermolysis chamber 210. The original post was a media without fox news.

In certain preferred embodiments of the present invention, the apparatus includes a reaction vessel 200' defining a separation chamber 216 configured for direct communication with an upper portion of the thermolysis chamber 210. The separation chamber 216 may comprise a fractioning and/or rectification column having at least one tray 218. A product stream comprising at least one organic acid product is withdrawn by a product stream line 220 through an outlet defined by an upper section of the separation chamber 216. A portion of product stream may be cooled and returned to the at least one tray 218 of the separation chamber 216. A condensate may flow out of the bottom of the separation chamber 216 and return comprising a mixture of polylactone oligomers to the thermolysis chamber 210 for thermolysis. The product stream comprising at least one organic acid product may undergo cooling and further processing. The processing may include additional purification to remove by-products, unrelated feed components and other impurities.

The reaction vessel 200' also includes a heater 222 to provide heat for endothermic conversion of the at least one polylactone product to at least one organic acid product. FIG. 3 shows a heater 222 in the form of a heating jacket that surrounds a lower portion of the thermolysis chamber 210. In alternate embodiments, the heater 222 may be an external heat exchanger connected to the thermolysis chamber 210 with a pump-around loop for circulation of hot fluid. In the embodiment of FIG. 3 a hot fluid stream influent line 224 delivers hot fluid to the heater 222 and a hot fluid stream effluent line 226 removes hot fluid from the heater 222. Suitable fluids include hot oil and molten salts.

In certain preferred embodiments, the reaction vessel 200' may define a slip stream outlet 228 which may direct polylactone oligomers of a variety of chain lengths, residual polymerization initiator, radical polymerization inhibitor, and/or radically polymerized organic acid of a variety of chain lengths to a bottoms squeezer 230. The bottoms squeezer 230 is a reactive distillation vessel such as a thin film evaporator for thermolysis of polylactone oligomers into volatile species like at least one organic acid product and polylactone oligomers of a variety of chain lengths. The bottoms squeezer 230 is connected to a bottoms squeezer heater 232 for heating the contents of the bottoms squeezer 230. The volatile species are withdrawn from the bottoms squeezer 230 through a bottoms squeezer condenser 234 by a vacuum source 236 and returned to the thermolysis chamber 210 or mixed with the product stream 220. The volatile species like at least one organic acid product are returned to the thermolysis chamber 210 by a recycle stream inlet 238. The liquid residence time in the bottoms squeezer 230 may be between 5 seconds and 3 hours, depending upon flow conditions and operating temperature, but is preferably 10-30 minutes. Less volatile and non-decomposable species such as residual polymerization initiator, radical polymerization inhibitor, and radically polymerized poly organic acid are removed from the bottoms squeezer by a purge stream line 240'. Additionally, polylactone oligomers of a variety of chain lengths, residual polymerization initiator, radical polymerization inhibitor, and/or radically polymerized poly organic acid, such as polyacrylic acid, of a variety of chain lengths may be removed directly from the thermolysis chamber 210 by a purge stream line 240'.

The reaction vessel 200' illustrated in FIG. 3 is configured to included mechanical mixing. A mechanical mixer 246 may be rotated by a motor 248 so that at least one blade 250 provides mechanical mixing to the material in the retaining volume of the thermolysis chamber 210.

Figure 4:
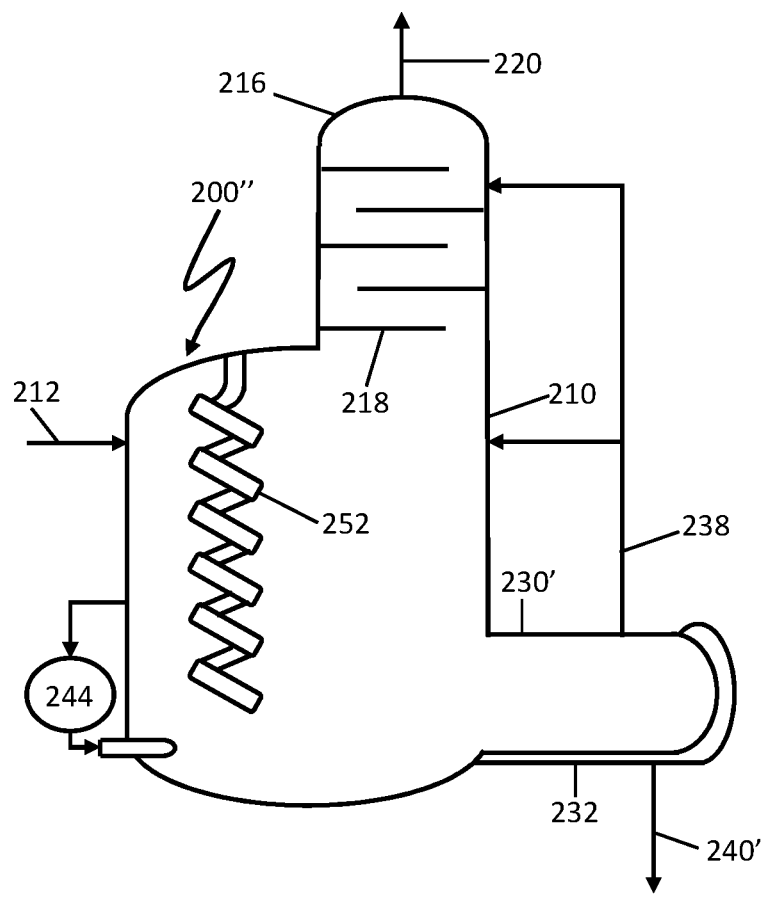
FIG. 4 illustrates another preferred embodiment including a reaction vessel for thermolysis.

FIG. 4 illustrates another preferred embodiment of a reaction vessel 200" configured for continuous flow. The reaction vessel 200" includes a thermolysis chamber 210 sized and shaped to define a feed stream inlet 212 for receiving a feed stream comprising at least one polylactone products. The thermolysis chamber 210 is in direct communication with a separation chamber 216 connected to a product stream line 220 at the top of the separation chamber 216. The separation chamber 216 is a rectification column with at least one trays 218. In FIG. 4, a heating coil 252 has heat exchange tubes through which hot liquid or gas may be circulated for providing heat internally to the feed stream. The retaining volume of the thermolysis chamber 210 is also in direct communication with a bottoms squeezer 230' so that polylactone oligomers of a variety of chain lengths, residual polymerization initiator, radical polymerization inhibitor, and/or radically polymerized poly organic acid of a variety of chain lengths may be heated under thermolysis conditions. The bottoms squeezer 230' is connected to a bottoms squeezer heater 232 for thermolyzing small chain polylactone oligomers and distilling at least one organic acid product to be returned to the separation chamber 216 by a recycle stream inlet 238. Less volatile materials such as residual polymerization initiator, radical polymerization inhibitor, and/or radically polymerized poly organic acid of a variety of chain lengths may be removed by a purge stream line 240'. The contents of the thermolysis chamber 210 are mixed by a jet mixer 244 which may remove liquid from the retaining volume of the thermolysis chamber 210 and return the liquid to the retaining volume of the thermolysis chamber 210 such as with a pump.

In certain embodiments, such as the embodiment illustrated in FIG. 4, it may be preferable to withdraw the product stream comprising at least one organic acid products in a vapor phase. The separation chamber 216 illustrated in FIG. 4 may cause the feed stream in vapor phase to undergo condensation and/or distillation to remove higher-boiling and/or lower-boiling impurities. In some embodiments, if distillation is required to remove higher-boiling impurities, then polymerization inhibitor may be introduced to any liquid phase organic acid, for example, in the thermolysis camber 210 and/or the separation chamber 216. In some embodiments, if 4-methoxyphenol is used as a polymerization inhibitor, the concentration of dissolved oxygen may be managed oxygen gas or oxygen mixed with an inert gas may be delivered to the thermolysis chamber. The bottom portions from the separation chamber 216 shall optimally be returned to the thermolysis chamber 210 for further thermolysis. In some embodiments, the separation chamber 216 may reduce the partial pressure of organic acid and the concentration organic acid in the reaction vessel's liquid contents. In another example, said vapors may be expelled from the product stream outlet when the partial pressure of organic acid is above a defined amount.

In some embodiments, such as the FIG. 4 illustrated embodiment, the bottoms squeezer 230' may be a reactive distillation vessel, such as a thin film evaporator either oriented vertically or horizontally, or a continuous agitated-tank reactor followed by a condenser (not shown in FIG. 4). The bottoms squeezer 230' may be operated at a temperature preferably in excess of 100° C., but may also be heated along its length to a higher temperature, cooled immediately to a lower temperature, and/or cooled along the length of the bottoms squeezer 230' to a lower temperature. The bottoms squeezer 230' may generally be operated below atmospheric pressure. The liquid residence time in the bottoms squeezer may be between 30 seconds and 30 hours, depending upon feed conditions and operating temperature, but preferably 2-15 minutes.

In certain embodiments, the residual waste stream purged from the at least one reaction vessel may include, for example, high boiling organics (or organic heavies), for example, resulting from the polymerization catalyst and succinic anhydride, as well as the cationic and anionic carbonylation catalyst species if the carbonylation catalyst was not separated prior to thermolysis. In some embodiments, the high boiling organics (or organic heavies) may include any compounds which are not the at least one organic acid product. In certain embodiments, the high boiling organics (or organic heavies) may include any compounds which remain in a bottoms stream after condensing the at least one organic acid product. In some embodiments, the high boiling organics (or organic heavies) may include polymerization catalyst, or carbonylation catalyst or components thereof (for example, organic compounds from the carbonylation catalyst).

In some embodiments, the at least one reaction vessel defining a thermolysis chamber is a fluidized bed reactor. In some embodiments, inert gas may be used to fluidize inert solid heat transfer medium and heat the at least one polylactone product that are fed into the thermolysis chamber. In some embodiments, the at least one polylactone product may be fed into the thermolysis chamber in molten form, for example, via a spay nozzle. In some embodiments, the molten form may help facilitate the dispersion of the at least one polylactone product inside the thermolysis chamber.

In some embodiments, the at least one reaction vessel defining a thermolysis chamber may be equipped with a cyclone that returns heat transfer medium solid back to the thermolysis chamber. An inert gas, at least one organic acid product, and higher boiling impurities (such as substituted succinic anhydride and/or substituted acrylic acid dimer) are fed from the cyclone to a partial condenser where impurities are separated. For example, the condenser may be used to condense the high boiling impurities, and such impurities can then be purged from the at least one reaction vessel as a residual waste stream.

In other embodiments, the at least one reaction vessel include a moving bed reactor. At least one polylactone product may be fed into the moving bed reactor as a solid and at least one organic acid products may exit the moving bed reactor as a vapor stream which may condensed.

In certain preferred embodiments, the reactor systems and processes of the present invention may include heating the at least one polylactone product to a temperature in a thermolysis chamber from about 150° C. to about 300° C., from about 150° C. to about 200° C., from about 150° C. to about 250° C., from about 175° C. to about 300° C., from about 200° C. to about 250° C., from about 225° C. to about 275° C., from about 250° C. to about 300° C., from about 200° C. to about 300° C., from about 200° C. to about 400° C., or from about 200° C. to about 500° C. In some variations, operating temperature is the average temperature of the contents of the thermolysis chamber.

In some variations, the operating pressure in the thermolysis chamber is from about 0.01 atmospheres to about 500 atmospheres (absolute), from about 0.01 atmospheres to about 10 atmospheres (absolute), from about 0.01 atmospheres to about 50 atmospheres (absolute), from about 1 atmosphere to about 10 atmospheres (absolute), from about 1 atmosphere to about 50 atmospheres (absolute), from about 1 atmosphere to about 100 atmospheres (absolute), from about 10 atmospheres to about 50 atmospheres (absolute), from about 10 atmospheres to about 100 atmospheres (absolute), from about 50 atmospheres to about 100 atmospheres (absolute), from about 50 atmospheres to about 200 atmospheres (absolute), from about 100 atmospheres to about 200 atmospheres (absolute), from about 100 atmospheres to about 250 atmospheres (absolute), from about 200 atmospheres to about 300 atmospheres (absolute), from about 200 atmospheres to about 500 atmospheres (absolute), or from about 250 atmospheres to about 500 atmospheres (absolute).

In preferred embodiments, at least one polylactone product stream enters at least one reaction vessel defining a thermolysis chamber, either in solid or liquid phase at a temperature between 100° C. and 320° C., and absolute pressure between 1 mmHg and 5000 mmHg. In certain preferred embodiments, the reactor systems and processes of the present invention provide for heat transfer input, for example internal coils, external heat exchanger with a pump-around loop from and back to at least one reaction vessel, or a baffled jacket on the walls of the at least one reaction vessel. Alternatively, a high temperature liquid or gas that that does not significantly affect the reaction chemistry may be introduced to maintain desired reaction temperature and separated downstream. Depending upon time and temperature residence time for complete conversion may vary from a few seconds to 24 hours or more. Mixing of the contents of the reactor may also improve mass and heat transfer.

In preferred embodiments, the reactor systems and processes of the present invention may provide for thermolysis conditions and certain configurations that will minimize the loss of the at least one organic acid product. For example, the reactor systems and processes of the present invention may include the use of a depolymerization catalyst to decrease required reaction severity and/or use radical polymerization inhibitor. Advantageously, the depolymerization catalyst may be at least one salt of the at least one organic acid product.

In certain preferred embodiments, the reactor systems and processes of the present invention can minimize the concentration of the at least one organic acid product in the liquid phase, for example, by removing vapors from the headspace of the at least one reaction vessel and lowering the at least one organic acid product's partial pressure in the headspace. Sparging with an inert gas, preferably continuously will further reduce the concentration of the at least one organic acid product in the reactor's liquid contents. Withdrawal of liquid effluent stream and any other nonvolatile components may also be desired to manage accumulation of unwanted polymers. These may be directed to a second thermolysis reactor, to waste treatment, or to a reactive distillation to convert the considerable polylactone in the stream to volatile species such as at least one organic acid product. The vapor effluent from this distillation operation can flow back to the primary reactor, or be mixed with the vapor effluent from the primary reactor.

In some embodiments, the reactor systems and processes perform thermolysis under an oxygen and water free atmosphere. For example, in certain variations, the amount of oxygen present in the thermolysis reactor is less than 1 wt %, less than 0.5 wt %, less than 0.01 wt %, or less than 0.001 wt %. In certain variations, the amount of water present in the thermolysis reactor is less than 1 wt %, less than 0.5 wt %, less than 0.01 wt %, or less than 0.001 wt %.

In certain preferred embodiments, the reactor systems and processes of the present invention include configurations and steps to manage and integrate heat produced. Advantageously, heat produced during certain steps and/or in certain reaction vessels may be transferred to other steps and/or reaction vessels minimizing reliance on external heat sources. The carbonylation reaction which occurs during certain steps and the polymerization reaction which occurs during certain steps are exothermic. The heat generated from exothermic reactions, such as from a reaction vessel defining a carbonylation chamber and/or polymerization chamber, can be captured and used, such as by retaining the heat within a heat transfer medium and directing the heat transfer medium to a reaction vessel with thermolysis chamber for thermolysis. For example, in some variations of the reactor systems and processes provided herein, steam may be generated in heat transfer equipment (e.g., shell and tube heat exchanger and reactor cooling jacket) via a temperature gradient between process fluid and water/steam. In other embodiments of the reactor systems and processes provided herein, other suitable heat transfer fluids may be used.

In certain embodiments of the present invention, the components of the reactor system may be in two or more locations which are remote from each other. In some embodiments, at least one reaction vessel defining a polymerization chamber may be in a location remote from at least one reaction vessel defining a thermolysis chamber. In other embodiments, at least one reaction vessel defining a carbonylation chamber may be in a location remote from at least one reaction vessel defining a polymerization chamber which may be in a location remote from at least one reaction vessel defining a thermolysis chamber.

In certain embodiments, reactor systems and processes of the present invention are characterized in that the location where the at least one polylactone product are produced (i.e. the first location) and the location where at least a portion of the at least one polylactone product undergoes thermolysis to produce at least one organic acid (i.e. the second location) are at least 10 miles apart. In certain embodiments, the first location and the second location are between 100 and 12,000 miles apart. In certain embodiments, the first location and the second location are at least, 250 miles, at least 500 miles, at least 1,000 miles, at least 2,000 or at least 3,000 miles apart. In certain embodiments, the first location and the second location are between about 250 and about 1,000 miles apart, between about 500 and about 2,000 miles apart, between about 2,000 and about 5,000 miles apart, or between about 5,000 and about 10,000 miles apart. In certain embodiments, the first location and the second location are in different countries.

In certain embodiments, the first location and the second location are on different continents. Price differences between different locations can make it advantageous to form the at least one polylactone product at one location, and to liberate the at least one organic acid product at a different location. The ability to safely store and transport the at least one polylactone product enables the formation of the at least one polylactone product at a first location where the cost of raw materials is less than at a second location, followed by transportation to the second location and subsequent thermolysis to liberate the at least one organic acid product.

The embodiments described herein are not intended to be limited to the aspects shown, but are to be accorded the widest scope consistent with the principles and features disclosed herein.

What is claimed is:

1. A process for producing an organic acid product, wherein the process comprises:
   a. introducing epoxide reagent and carbon monoxide reagent to a reaction vessel through a feed stream inlet, the reaction vessel comprising a separation chamber positioned above and in direct communication with a thermolysis chamber;
   b. contacting the epoxide reagent and the carbon monoxide reagent with a carbonylation catalyst to produce a beta-lactone intermediate;
   c. polymerizing the beta-lactone intermediate with a polymerization initiator in the presence of a metal cation to produce a polylactone product; and
   d. heating the polylactone product under thermolysis conditions to produce the organic acid product.

2. The process of claim 1, wherein the epoxide reagent comprises ethylene oxide, propylene oxide, 1,2-epoxyhexane, 1,2-epoxydodecane, 3,4-epoxy-1-butene, 1,2-epoxy-5-hexene, 1,2-epoxy-9-decene, isoprene monoxide, epichlorohydrin, 1,3-butadiene diepoxide, 1,2,7,8-diepoxyoctane, 1,2-epoxycyclopentane, or cyclooctene oxide.

3. The process of claim 1, wherein the epoxide reagent and the carbon reagent enter the reaction vessel with mechanical assistance.

4. The process of claim 1, wherein a mechanical pump assists in introducing the epoxide reagent and the carbon monoxide reagent to the reaction vessel.

5. The process of claim 1, wherein the epoxide reagent and the carbon monoxide reagent are stored at a higher atmospheric pressure than the reaction vessel defining a carbonylation chamber.

6. The process of claim 1, wherein the carbonylation catalyst comprises a metal carbonyl-Lewis acid catalyst.

7. The process of claim 1, wherein the carbonylation catalyst is introduced to the reaction vessel before introducing the carbon monoxide reagent and the epoxide reagent.

8. The process of claim 1, wherein the carbonylation catalyst comprises a neutral metal carbonyl compound.

9. The process of claim 1, wherein the polymerization initiator has a general formula of M"X where M" is cationic and X is anionic.

10. The process claim 1, wherein the polymerization initiator comprises a carboxylate salt.

11. The process of claim 1, wherein the polylactone product undergoes thermolysis continuously.

* * * * *